US009317664B2

(12) United States Patent
Ahuja et al.

(10) Patent No.: US 9,317,664 B2
(45) Date of Patent: Apr. 19, 2016

(54) METHOD AND DEVICE FOR PARTITIONING A MOLECULE

(75) Inventors: Sachin Ahuja, Menlo Park, CA (US); David Kita, Milpitas, CA (US); Eniko Fodor, Fremont, CA (US); Adityo Prakash, Fremont, CA (US)

(73) Assignee: VERSEON CORPORATION, Fremont, CA (US)

( * ) Notice: Subject to any disclaimer, the term of this patent is extended or adjusted under 35 U.S.C. 154(b) by 2012 days.

(21) Appl. No.: 10/966,041

(22) Filed: Oct. 14, 2004

(65) Prior Publication Data

US 2005/0228592 A1 Oct. 13, 2005

Related U.S. Application Data

(60) Provisional application No. 60/511,189, filed on Oct. 14, 2003.

(51) Int. Cl.

| G01N 33/48 | (2006.01) |
|---|---|
| G01N 33/50 | (2006.01) |
| G06F 19/00 | (2011.01) |
| G06F 19/24 | (2011.01) |
| G06F 19/26 | (2011.01) |
| G06F 19/28 | (2011.01) |
| G01N 33/68 | (2006.01) |
| G06F 19/16 | (2011.01) |
| C40B 30/02 | (2006.01) |
| G06F 19/18 | (2011.01) |

(52) U.S. Cl.
CPC .......... *G06F 19/706* (2013.01); *G01N 33/6803* (2013.01); *G06F 19/16* (2013.01); *G06F 19/24* (2013.01); *G06F 19/26* (2013.01); *G06F 19/28* (2013.01); *C40B 30/02* (2013.01); *G06F 19/18* (2013.01); *G06F 19/701* (2013.01); *G06F 19/707* (2013.01)

(58) Field of Classification Search
None
See application file for complete search history.

(56) References Cited

U.S. PATENT DOCUMENTS

| 5,241,663 A * | 8/1993 | Rohwer ........................ 711/172 |
| 5,404,454 A * | 4/1995 | Parks ............................. 710/21 |
| 6,496,366 B1 * | 12/2002 | Coglitore et al. ........ 361/679.46 |
| 2002/0127608 A1 | 9/2002 | Cardozo et al. |
| 2003/0065448 A1 | 4/2003 | Cramer et al. |

FOREIGN PATENT DOCUMENTS

| JP | 08-285757 | 11/1996 |
| JP | 2003-206246 | 7/2003 |

OTHER PUBLICATIONS

Rarey et al. Feature trees: A new molecular similarity measure based on tree matching. Journal of Computer-Aided Molecular Design, vol. 12, 1998, p. 471-490.*
Smith TJ. MolView: A program for analyzing and displaying atomic structures on the Macintosh personal computer. Journal of Molecular Graphics. vol. 13, 1995, pp. 122-125.*
Lewell et al. RECAP—Retrosynthetic Combinatorial Analysis Procedure: A powerful new technique for identifying privileged molecular fragments with useful applications in combinatorial chemistry. J. Chem. Inf. Comput. Sci. 1998, vol. 38, pp. 511-522.*
Brooks et al. CHARMM: A program for macromolecular energy, minimization, and dynamics calculations. Journal of Computational Chemistry. vol. 4, 1983, pp. 187-217.*
Sheinerman et al. On the role of electrostatic interactions in the design of protein-protein interfaces. Journal of Molecular Biology. 2002, vol. 318, pp. 161-177.*
Wise et al. Peptide-mass fingerprinting and the ideal covering set for protein characterisation. Electrophoresis, 1997, vol. 18, pp. 1399-1409.*
Klinger V. DiPaCS; A new concept for parallel circuit simulation. Simulation Symposium 1995, pp. 32-41.*
Koubogiannis et al. Solution of flow problems using unstructured grids on distributed memory platforms. Comput. Methods Appl. Mech. Engrg., vol. 160, 1998, pp. 89-100.*
Lascaris et al. DNA binding requirements of the yeast protein Rap1p as selected in silico from ribosomal protein gene promoter sequences. Bioinformatics, 1999, vol. 15, pp. 267-277.*
Restriction Enzymes: Bam HI. obtained online on Jun. 2, 2009 from fermentas.com/catalog/re/bamhi.htm.*
Cho et al. Binary formal inference-based recursive modeling using multiple atom and physicochemical property class pair and torsion descriptors as decision criteria. Journal of Chemical Information and Computer Sciences. 2000, vol. 40, pp. 668-680.*
Ewing et al. DOCK 4.0: Search strategies for automated molecular docking of flexible molecule databases. Journal of Computer-Aided Molecular Design. vol. 15, 2001, pp. 411-428.*
Babad JM. A record and filed partitioning model. Communications of the ACM, vol. 20, 1977, pp. 22-31.*
Schneider et al. Matrix-assisted Laser Desorption Mass Spectrometry of Homopolymer Oligodeoxyribonucleotides. Influence of base composition on the mass spectrometric response. Organic Mass Spectrometry, 1993, vol. 28, pp. 1353-1361.*
Beckers, et al., "Parallel Processing of Chemical Information in a Local Area Network-III. Using Genetic Algorithms For Conformational Analysis of Biomacromolecules," Computer & Chemistry, Elsevier UK, vol. 20, No. 4, 1996, pp. 449-457.
Hendrickson, et al., "Graph partitioning models for parallel computing," Parallel Computing, Elsevier Publishers, Amsterdam, NL, vol. 26, No. 12, Nov. 2000, pp. 1519-1534.

(Continued)

*Primary Examiner* — Russell S Negin
(74) *Attorney, Agent, or Firm* — Davis Wright Tremaine LLP; Philip H. Albert

(57) ABSTRACT

A method for partitioning a molecular subset is described. The partitioning method takes into account molecular structure and its manner of storage and transmission, transformations to be applied to the molecular subset and their implementation, and constraints imposed by the implementation of the partitioning method. Using this method, a molecular subset can be stored, transmitted, and processed more efficiently. The resulting efficiency makes it possible to design and run applications which require complex molecular processing, such as rational drug discovery, virtual library design, etc.

58 Claims, 29 Drawing Sheets

(56) References Cited

OTHER PUBLICATIONS

Schloegel, et al., Graph Partitioning for High-Performance Scientific Simulations [online] 2000, pp. 1-39, Retrieved from Internet: URL:http://citeseer.ist.psu.edu/cache/papers/cs/15308/http:zSzzSzwww-users.itlabs.umn.eduzSz{karypiszSzpublicationszSzPaperszSzPDFzSzgpchapter.pdf/sch1oege1009raph.pdf>[retrieved on Dec. 21, 2007].

European Search Report EP 04 79 5331, dated Jan. 18, 2008.

Perlman, D. A., et al., "AMBER, A Package of Computer Programs for Applying Molecular Mechanics, Normal Mode Analysis, Molecular Dynamics and Free Energy Calculations to Simulate the Structural and Energetic Properties of Molecules," Computer Physics Communications, Sep. 2, 1995, vol. 91, pp. 1-41.

Lamb, Michelle, L., et al., "Design, Docking, and Evaluation of Multiple Libraries Against Multiple Targets," PROTEINS: Structure, Function, and Genetics, 2000, vol. 42, No. 3, pp. 296-318.

Trelles, Oswaldo, "On the Parallelisation of Bioinformatics Applications." Briefings in Bioinformatics, May 2001, vol. 2, No. 2, pp. 181-194.

English Translation of Office Action mailed on Jun. 14, 2011 in related Japanese Patent Application No. 2006-535364, 3 pages.

Examination Report issued by the Canadian Intellectual Property Office in CA Patent Application No. 2,542,343, mailed on Nov. 16, 2015, 9 pages.

* cited by examiner

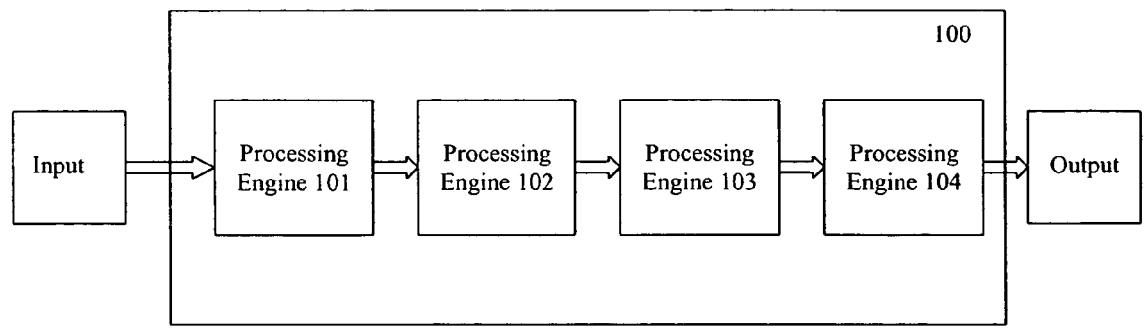
Figure 1: General processing pipeline

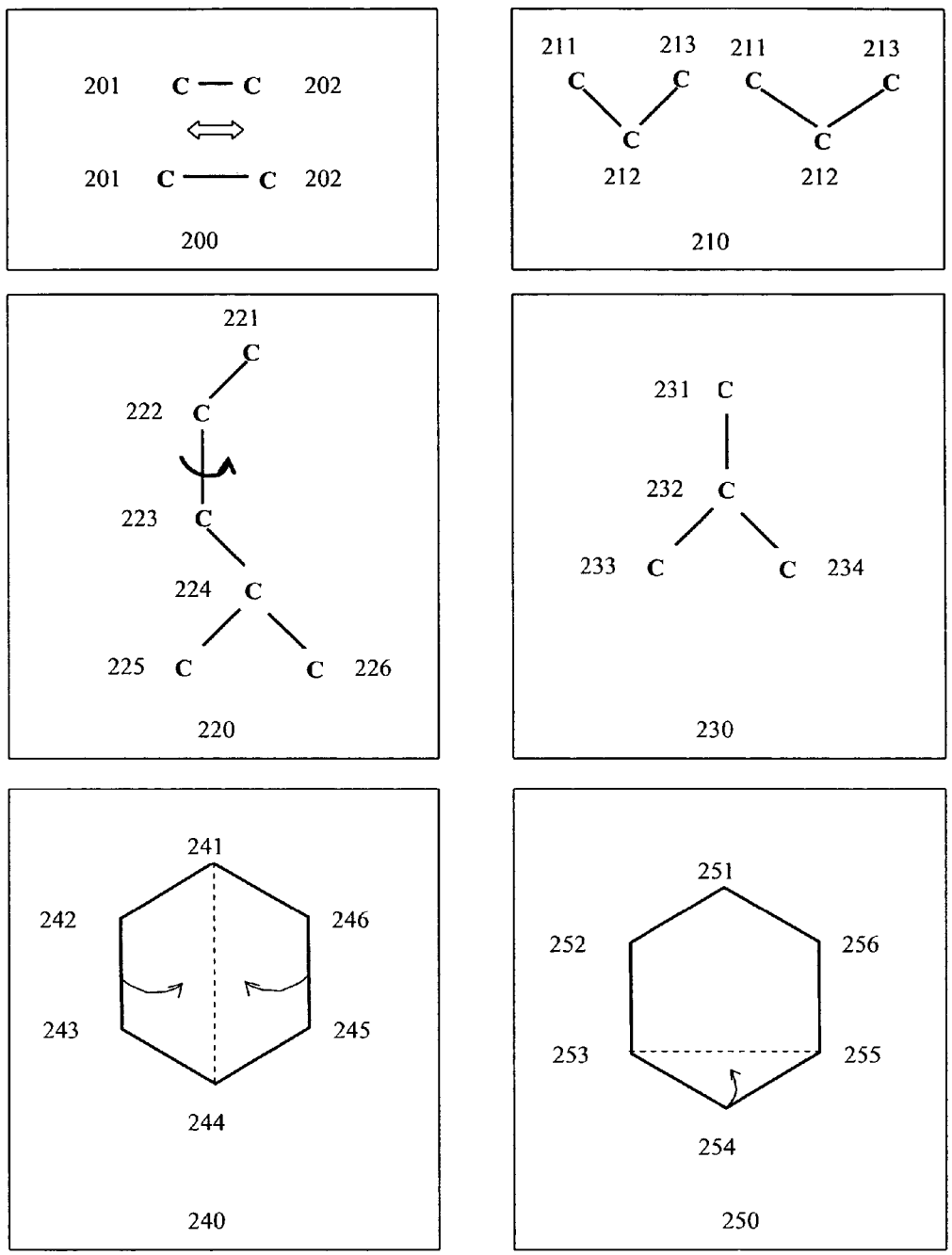
Figure 2: Illustration of some of the degrees of freedom

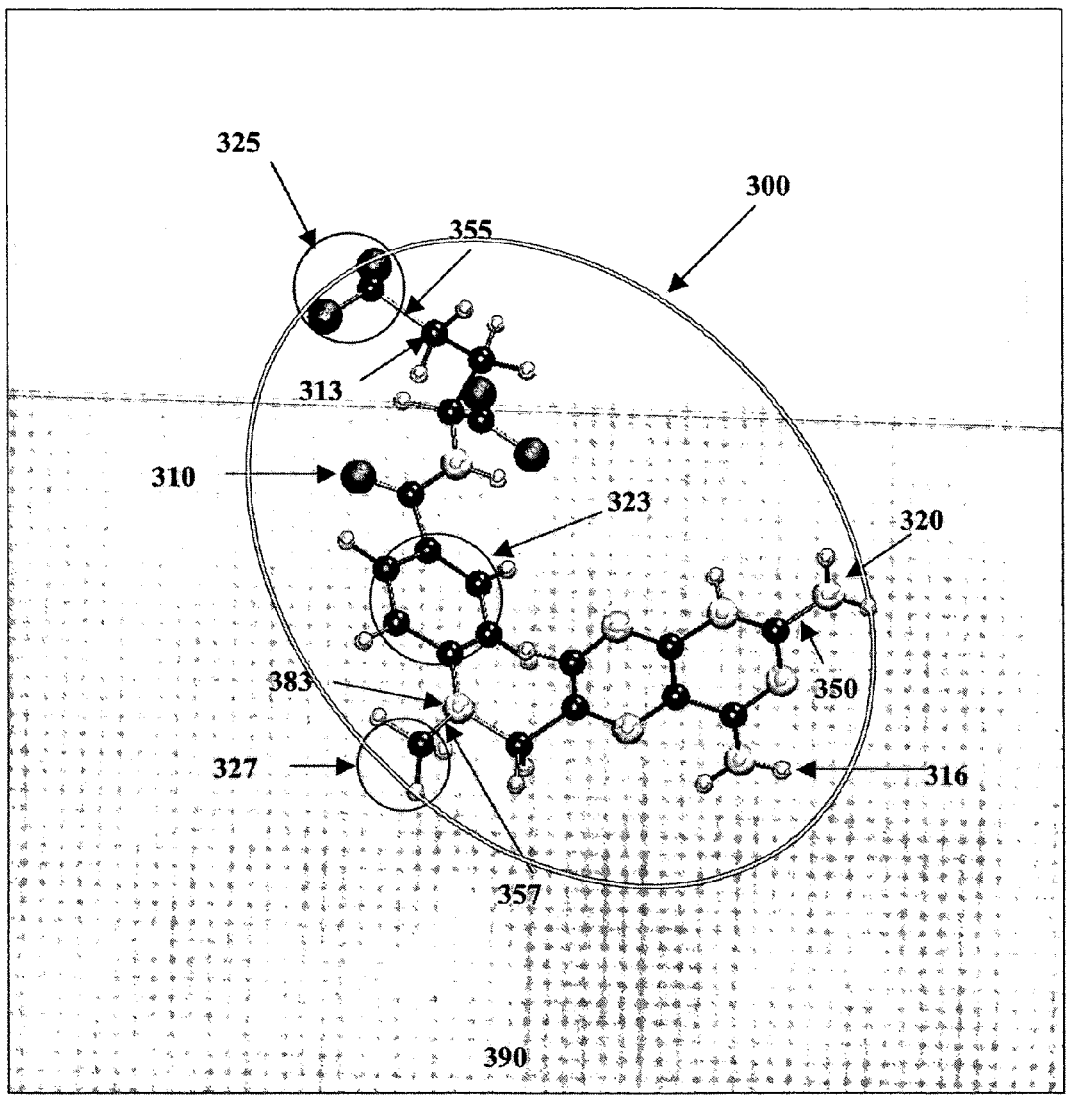
Figure 3a: Ball-and-stick representation of methotrexate

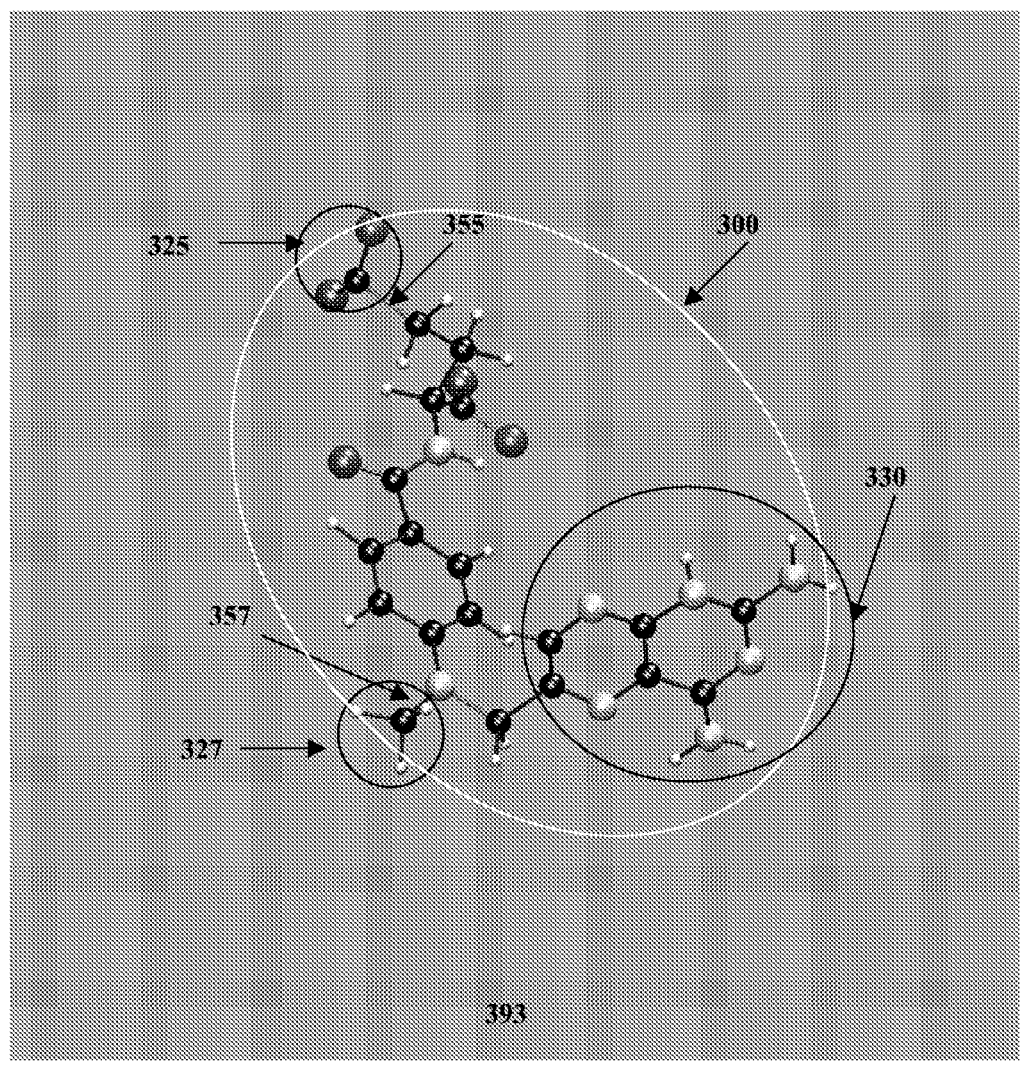
Figure 3b: Methotrexate – new conformation due to dihedral rotation about 355 and 357

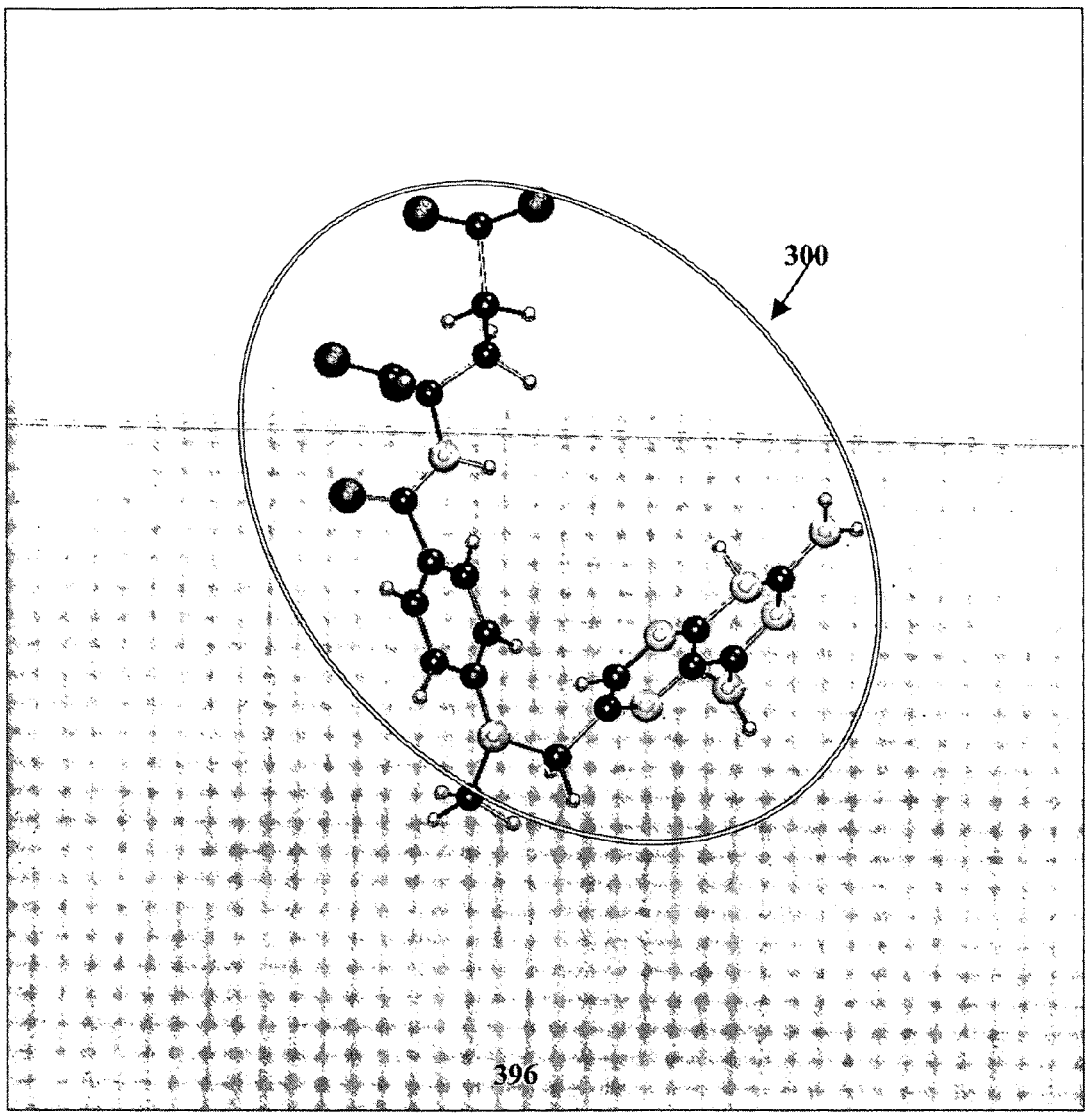
Figure 3c: Methotrexate – new conformation due to dihedral rotation about all rotatable bonds

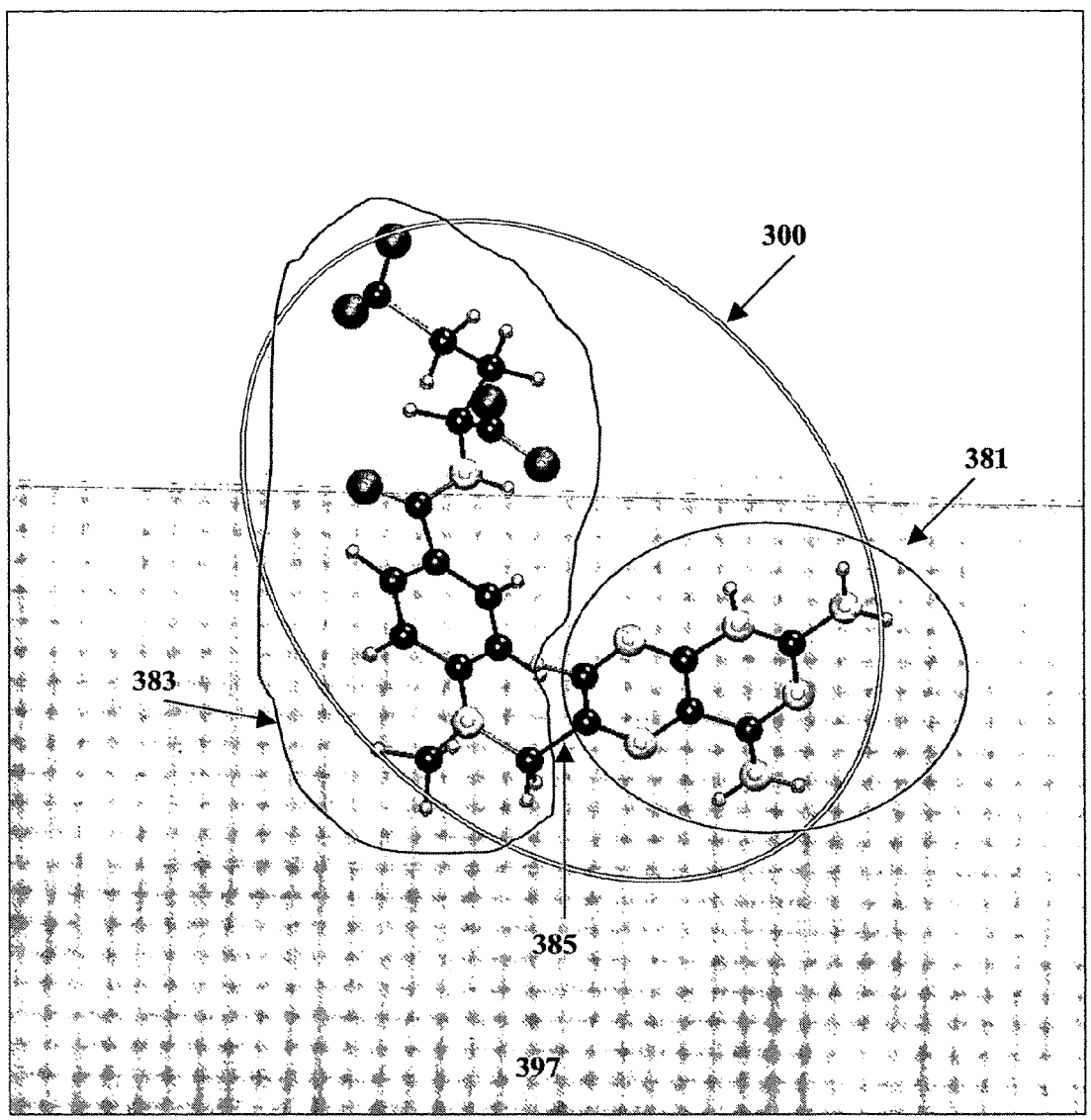
Figure 3d: Methotrexate – Group of atoms 381 changes coordinates due to rotation about bond 385. Group of atoms 383 is invariant with respect to rotation about bond 385

```
HEADER    OXIDO-REDUCTASE                              25-JUN-82           4DFR
COMPND    DIHYDROFOLATE REDUCTASE (E.C.1.5.1.3) COMPLEX WITH METHOTREXATE
SOURCE    (ESCHERICHIA COLI B)
JRNL      REF    J.BIOL.CHEM.                V. 257 13650 1982
FORMUL    (C20 H22 N8 O5)
HETATM  1    N1     MTX   A   1      22.983  58.667  24.488
HETATM  2    C2     MTX   A   1      23.468  58.215  23.282
HETATM  3    NA2    MTX   A   1      24.797  58.223  23.208
HETATM  4    N3     MTX   A   1      22.792  57.819  22.23
HETATM  5    C4     MTX   A   1      21.459  57.803  22.068
HETATM  6    NA4    MTX   A   1      20.821  57.44   21.075
HETATM  7    C4A    MTX   A   1      20.9    58.304  23.363
HETATM  8    N5     MTX   A   1      19.558  58.514  23.37
HETATM  9    C6     MTX   A   1      18.989  58.982  24.422
HETATM 10    C7     MTX   A   1      19.781  59.256  25.628
HETATM 11    N8     MTX   A   1      21.096  59.176  25.562
HETATM 12    C8A    MTX   A   1      21.608  58.594  24.363
HETATM 13    C9     MTX   A   1      17.465  59.006  24.451
HETATM 14    N10    MTX   A   1      16.957  59.967  25.533
HETATM 15    CM     MTX   A   1      16.225  59.184  26.643
HETATM 16    C11    MTX   A   1      18.122  64.1    25.805
HETATM 17    C12    MTX   A   1      17.288  63.511  26.732
HETATM 18    C13    MTX   A   1      16.845  62.195  26.688
HETATM 19    C14    MTX   A   1      17.32   61.452  25.68
HETATM 20    C15    MTX   A   1      18.141  62.098  24.672
HETATM 21    C16    MTX   A   1      18.518  63.414  24.738
HETATM 22    C      MTX   A   1      18.192  65.626  25.834
HETATM 23    O      MTX   A   1      17.516  66.28   26.783
HETATM 24    N      MTX   A   1      19.329  65.981  25.135
HETATM 25    CA     MTX   A   1      19.837  67.459  25.135
HETATM 26    CT     MTX   A   1      20.159  67.548  23.635
HETATM 27    O1     MTX   A   1      20.289  66.659  22.848
HETATM 28    O2     MTX   A   1      19.921  68.75   23.149
HETATM 29    CB     MTX   A   1      21.217  67.669  25.761
HETATM 30    CG     MTX   A   1      20.891  67.636  27.32
HETATM 31    CD     MTX   A   1      19.921  68.524  28.357
HETATM 32    OE1    MTX   A   1      19.413  68.371  29.593
HETATM 33    OE2    MTX   A   1      19.441  69.469  27.489
CONECT  1     2    12
CONECT  2     1     3     4
CONECT  3     2
CONECT  4     2     5
CONECT  5     4     6     7
CONECT  6     5
CONECT  7     5     8    12
CONECT  8     7     9
CONECT  9     8    10    13
CONECT 10     9    11
CONECT 11    10    12
CONECT 12     1     7    11
CONECT 13     9    14
CONECT 14    13    15    19
CONECT 15    14
CONECT 16    17    21    22
CONECT 17    16    18
CONECT 18    17    19
CONECT 19    14    18    20
CONECT 20    19    21
CONECT 21    16    20
CONECT 22    16    23    24
CONECT 23    22
CONECT 24    22    25
CONECT 25    24    26    29
CONECT 26    25    27    28
CONECT 27    26
CONECT 28    26
CONECT 29    25    30
CONECT 30    29    31
CONECT 31    30    32    33
CONECT 32    31
CONECT 33    31
END
```

Fig 4a: Molecular representation - PDB format

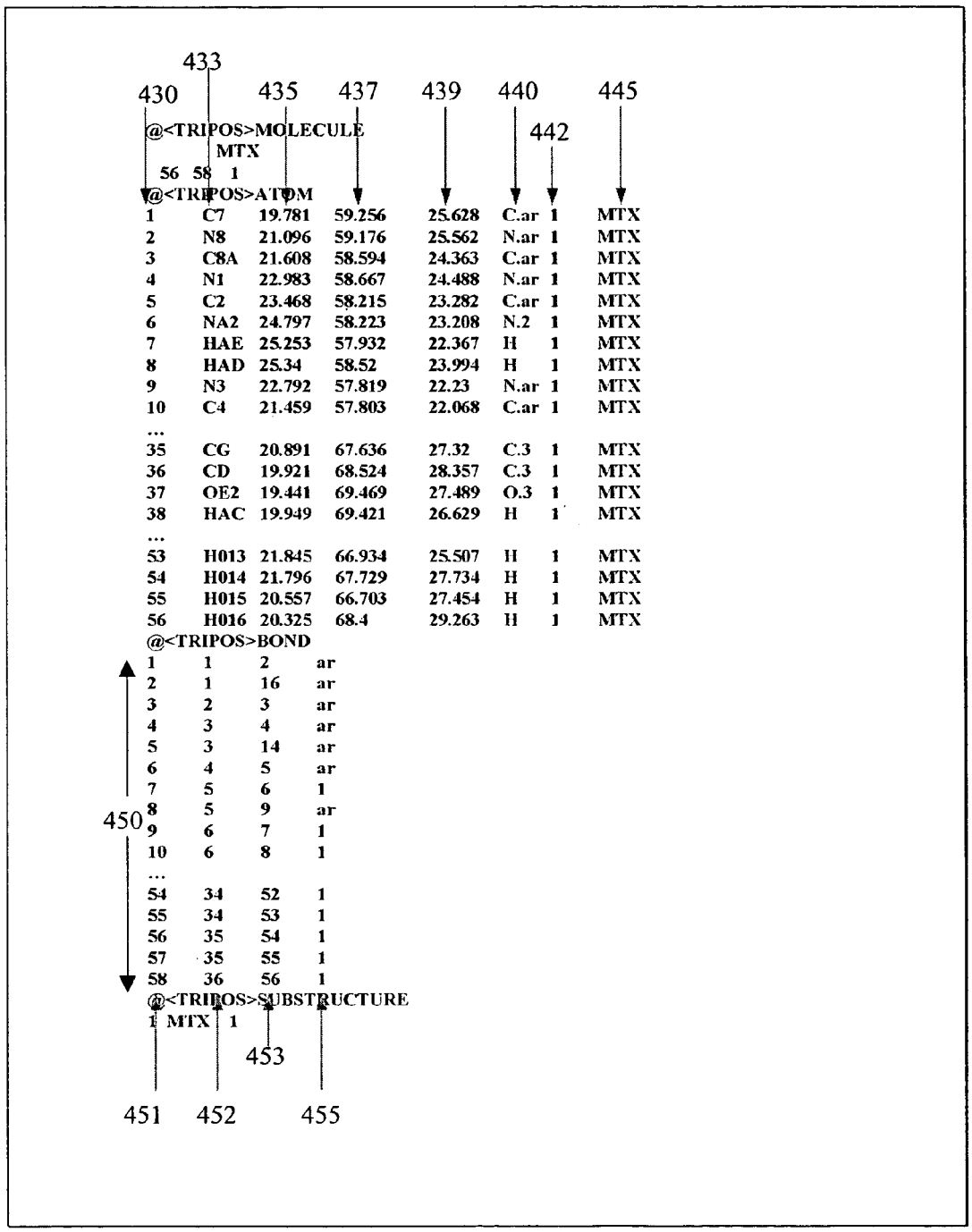
Fig 4b: Molecular representation – mol2 format

|       | 461 | 462 | 463 | 464 | 465 |
|-------|-----|-----|-----|-----|-----|

| 4dfr Atom | Amber Atom | Charge | Mass | VdW Radius | VdW Depth |
|---|---|---|---|---|---|
| N1 | NT | 0.1571 | 14.01 | 1.8240 | 0.1700 |
| C2 | CM | -0.0211 | 12.01 | 1.9080 | 0.0860 |
| NA2 | NT | 0.2746 | 14.01 | 1.8240 | 0.1700 |
| N3 | N2 | -0.3253 | 14.01 | 1.8240 | 0.1700 |
| C4 | CM | 0.0724 | 12.01 | 1.9080 | 0.0860 |
| NA4 | NT | 0.3867 | 14.01 | 1.8240 | 0.1700 |
| C4A | CD | -0.1444 | 12.01 | 1.9080 | 0.0860 |
| N5 | NC | -0.0303 | 14.01 | 1.8240 | 0.1700 |
| C6 | CM | -0.0100 | 12.01 | 1.9080 | 0.0860 |
| C7 | CM | -0.0582 | 12.01 | 1.9080 | 0.0860 |
| N8 | NC | 0.0543 | 14.01 | 1.8240 | 0.1700 |
| C8A | CM | -0.1038 | 12.01 | 1.9080 | 0.0860 |
| C9 | CT | -0.0544 | 12.01 | 1.9080 | 0.1094 |
| N10 | N2 | 0.0215 | 14.01 | 1.8240 | 0.1700 |
| CM | CT | -0.0805 | 12.01 | 1.9080 | 0.1094 |
| C11 | CA | -0.1230 | 12.01 | 1.9080 | 0.0860 |
| C12 | CA | -0.0146 | 12.01 | 1.9080 | 0.0860 |
| C13 | CA | -0.1936 | 12.01 | 1.9080 | 0.0860 |
| C14 | CA | -0.0392 | 12.01 | 1.9080 | 0.0860 |
| C15 | CA | -0.1960 | 12.01 | 1.9080 | 0.0860 |
| C16 | CA | -0.0365 | 12.01 | 1.9080 | 0.0860 |
| C | C | 0.2424 | 12.01 | 1.9080 | 0.0860 |
| O | O | -0.4167 | 16.00 | 1.6612 | 0.2100 |
| N | N | 0.0791 | 14.01 | 1.8240 | 0.1700 |
| CA | CT | -0.1036 | 12.01 | 1.9080 | 0.1094 |
| CT | C | 0.4000 | 12.01 | 1.9080 | 0.0860 |
| O1 | O2 | -0.7173 | 16.00 | 1.6612 | 0.2100 |
| O2 | O2 | -0.5761 | 16.00 | 1.6612 | 0.2100 |
| CB | CT | -0.0699 | 12.01 | 1.9080 | 0.1094 |
| CG | CT | -0.2188 | 12.01 | 1.9080 | 0.1094 |
| CD | C | 0.4453 | 12.01 | 1.9080 | 0.0860 |
| OE1 | O2 | -0.6396 | 16.00 | 1.6612 | 0.2100 |
| OE2 | O2 | -0.5993 | 16.00 | 1.6612 | 0.2100 |

Pitzer Potential: (PK/IDIVF) * (1 + cos(PN*phi - PHASE) )

| 4dfr Bond | Amber BOND | IDIVF | PK | PHASE | PN |
|---|---|---|---|---|---|
| O2-C -CT-N | X -C -CT-X | 4 | 0.00 | 0.0 | 2.0 |
| O2-C -CT-CT | X -C -CT-X | 4 | 0.00 | 0.0 | 2.0 |
| C -CT-CT-CT | X -CT-CT-X | 9 | 1.40 | 0.0 | 3.0 |
| CT-CT-CT-N | X -CT-CT-X | 9 | 1.40 | 0.0 | 3.0 |
| CT-CT-N -C | CT-CT-N -C | 1 | 0.53 | 0.0 | 1.0 |
| CA-C -N -CT | X -C -N -X | 4 | 10.00 | 180.0 | 2.0 |
| N -C -CA-CA | X -C -CA-X | 4 | 14.50 | 180.0 | 2.0 |
| CA-CA-N2-CT | X -CA-N2-X | 4 | 9.60 | 180.0 | 2.0 |
| H -CT-N2-CT | X -CT-N2-X | 6 | 0.00 | 0.0 | 3.0 |
| CM-CT-N2-CT | X -CT-N2-X | 6 | 0.00 | 0.0 | 3.0 |
| CM-CM-CT-N2 | X -CM-CT-X | 6 | 0.00 | 0.0 | 3.0 |

|     | 472 | 474 | 476 | 478 |
|-----|-----|-----|-----|-----|

Figure 4c: Amber96 forcefield descriptors for methotrexate

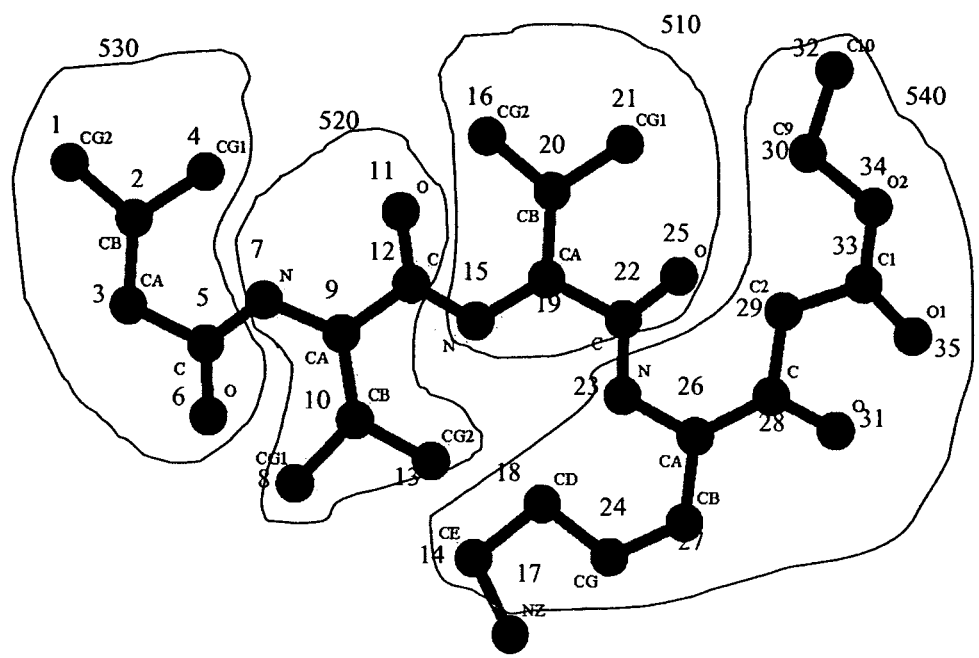
Figure 5a – Schematic representation of IVVL molecule

| | 501 | 502 | 503 | 504 | | |
|---|---|---|---|---|---|---|
| L1 | 1 | CG2 | IVA | 13.619 | 3.699 | 17.565 ... |
| L2 | 2 | CB | IVA | 14.811 | 3.832 | 18.483 ... |
| L3 | 3 | CA | IVA | 15.997 | 4.534 | 17.842 ... |
| L4 | 4 | CG1 | IVA | 14.378 | 4.66 | 19.691 ... |
| L5 | 5 | C | IVA | 17.154 | 4.737 | 18.842 ... |
| L6 | 6 | O | IVA | 17.21 | 4.079 | 19.924 ... |
| L7 | 7 | N | VAL | 18.049 | 5.609 | 18.482 ... |
| L8 | 8 | CG1 | VAL | 20.473 | 4.256 | 17.839 ... |
| L9 | 9 | CA | VAL | 19.236 | 5.882 | 19.338 ... |
| L10 | 10 | CB | VAL | 20.424 | 5.69 | 18.39 ... |
| L11 | 11 | O | VAL | 18.298 | 8.101 | 19.603 ... |
| L12 | 12 | C | VAL | 19.145 | 7.246 | 20.012 ... |
| L13 | 13 | CG2 | VAL | 20.312 | 6.625 | 17.164 ... |
| L14 | 14 | CE | LTA | 24.338 | 6.055 | 18.911 ... |
| L15 | 15 | N | VAL | 20.033 | 7.389 | 20.99 ... |
| L16 | 16 | CG2 | VAL | 18.016 | 8.175 | 22.968 ... |
| L17 | 17 | NZ | LTA | 24.252 | 4.93 | 19.891 ... |
| L18 | 18 | CD | LTA | 24.459 | 7.284 | 19.878 ... |
| L19 | 19 | CA | VAL | 20.15 | 8.659 | 21.739 ... |
| L20 | 20 | CB | VAL | 19.463 | 8.603 | 23.113 ... |
| L21 | 21 | CG1 | VAL | 19.516 | 9.981 | 23.831 ... |
| L22 | 22 | C | VAL | 21.661 | 8.992 | 21.823 ... |
| L23 | 23 | N | LTA | 22.103 | 9.879 | 20.933 ... |
| L24 | 24 | CG | LTA | 24.057 | 8.495 | 19.047 ... |
| L25 | 25 | O | VAL | 22.327 | 8.394 | 22.705 ... |
| L26 | 26 | CA | LTA | 23.55 | 10.21 | 20.947 ... |
| L27 | 27 | CB | LTA | 24.217 | 9.842 | 19.633 ... |
| L28 | 28 | C | LTA | 23.736 | 11.739 | 21.12 ... |
| L29 | 29 | C2 | LTA | 23.08 | 12.076 | 22.426 ... |
| L30 | 30 | C9 | LTA | 22.279 | 13.205 | 25.168 ... |
| L31 | 31 | O | LTA | 23.22 | 12.47 | 20.18 ... |
| L32 | 32 | C10 | LTA | 21.665 | 14.556 | 25.501 ... |
| L33 | 33 | C1 | LTA | 23.994 | 12.299 | 23.603 ... |
| L34 | 34 | O2 | LTA | 23.436 | 13.369 | 24.219 ... |
| L35 | 35 | O1 | LTA | 24.452 | 11.24 | 24.133 ... |

Fig 5b – An example list representation of IVVL molecule

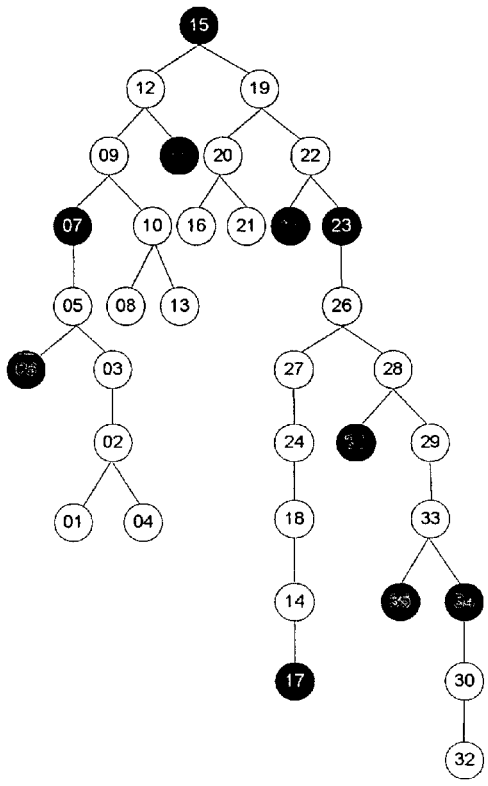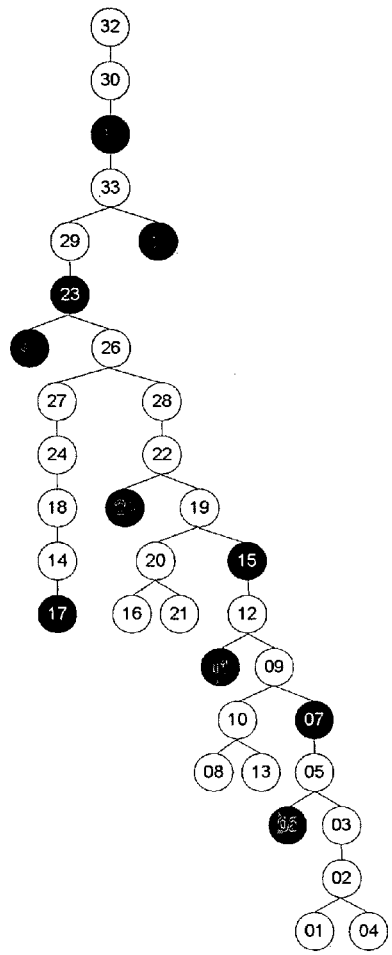
Fig 5c – An example tree representation of IVVL        Fig 5d – An example tree representation of IVVL

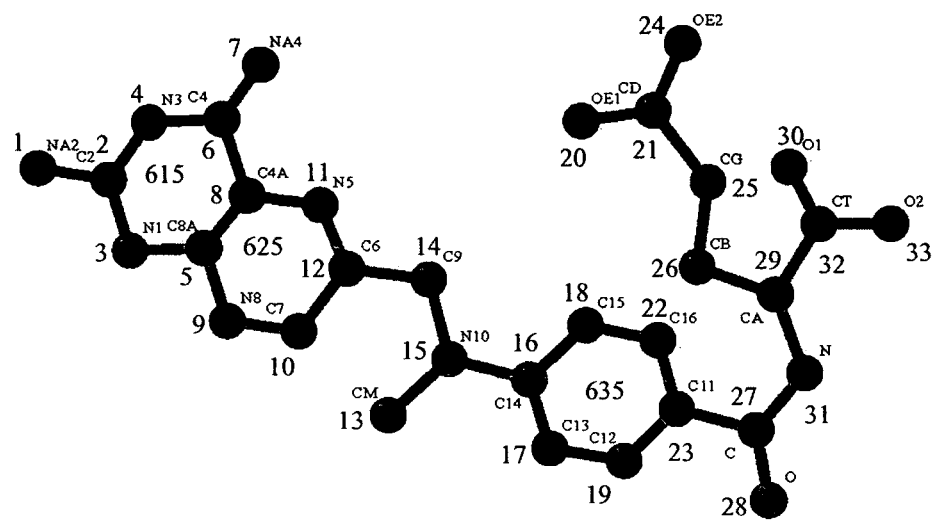
Fig 6a – Schematic of methotrexate molecule

|     | 601 | 602 | 603 | | 604 |
| --- | --- | --- | --- | --- | --- |
| L1  | 1   | NA2 | 14.808 | 64.996  47.270 | -0.44220 |
| L2  | 2   | C2  | 16.136 | 65.424  47.049 | 0.72560 |
| L3  | 3   | N1  | 16.724 | 65.101  45.857 | -0.44000 |
| L4  | 4   | N3  | 16.766 | 66.078  48.071 | -0.84410 |
| L5  | 5   | C8A | 17.991 | 65.747  45.644 | 0.46060 |
| L6  | 6   | C4  | 18.001 | 66.587  47.924 | 0.73800 |
| L7  | 7   | NA4 | 18.523 | 67.297  48.888 | -0.93090 |
| L8  | 8   | C4A | 18.630 | 66.369  46.644 | 0.07240 |
| L9  | 9   | N8  | 18.560 | 65.424  44.401 | -0.61120 |
| L10 | 10  | C7  | 19.725 | 66.102  44.371 | 0.37150 |
| L11 | 11  | N5  | 19.814 | 66.982  46.490 | -0.60290 |
| L12 | 12  | C6  | 20.308 | 66.821  45.261 | 0.25610 |
| L13 | 13  | CM  | 23.296 | 66.877  43.297 | 0.17240 |
| L14 | 14  | C9  | 21.711 | 67.394  45.048 | 0.15510 |
| L15 | 15  | N10 | 22.028 | 67.717  43.540 | -0.65270 |
| L16 | 16  | C14 | 21.189 | 68.492  42.724 | 0.10230 |
| L17 | 17  | C13 | 21.534 | 68.508  41.355 | -0.18720 |
| L18 | 18  | C15 | 20.168 | 69.307  43.231 | -0.17980 |
| L19 | 19  | C12 | 20.746 | 69.211  40.495 | -0.07200 |
| L20 | 20  | OE1 | 17.507 | 70.413  35.853 | -0.85950 |
| L21 | 21  | CD  | 16.286 | 70.898  36.272 | 0.91090 |
| L22 | 22  | C16 | 19.422 | 70.099  42.451 | -0.09110 |
| L23 | 23  | C11 | 19.702 | 69.969  41.061 | -0.13750 |
| L24 | 24  | OE2 | 15.722 | 72.117  36.236 | -0.84450 |
| L25 | 25  | CG  | 16.080 | 70.349  37.905 | -0.19490 |
| L26 | 26  | CB  | 15.656 | 71.197  39.259 | -0.08600 |
| L27 | 27  | C   | 18.966 | 70.777  40.090 | 0.66490 |
| L28 | 28  | O   | 19.469 | 71.019  39.002 | -0.58330 |
| L29 | 29  | CA  | 16.877 | 71.923  39.715 | 0.00170 |
| L30 | 30  | O1  | 16.202 | 72.626  41.863 | -0.98000 |
| L31 | 31  | N   | 17.735 | 71.051  40.429 | -0.52460 |
| L32 | 32  | CT  | 16.397 | 72.948  40.561 | 0.93190 |
| L33 | 33  | O2  | 15.866 | 74.111  40.362 | -0.76310 |

Fig 6b – An example list representation of methotrexate molecule

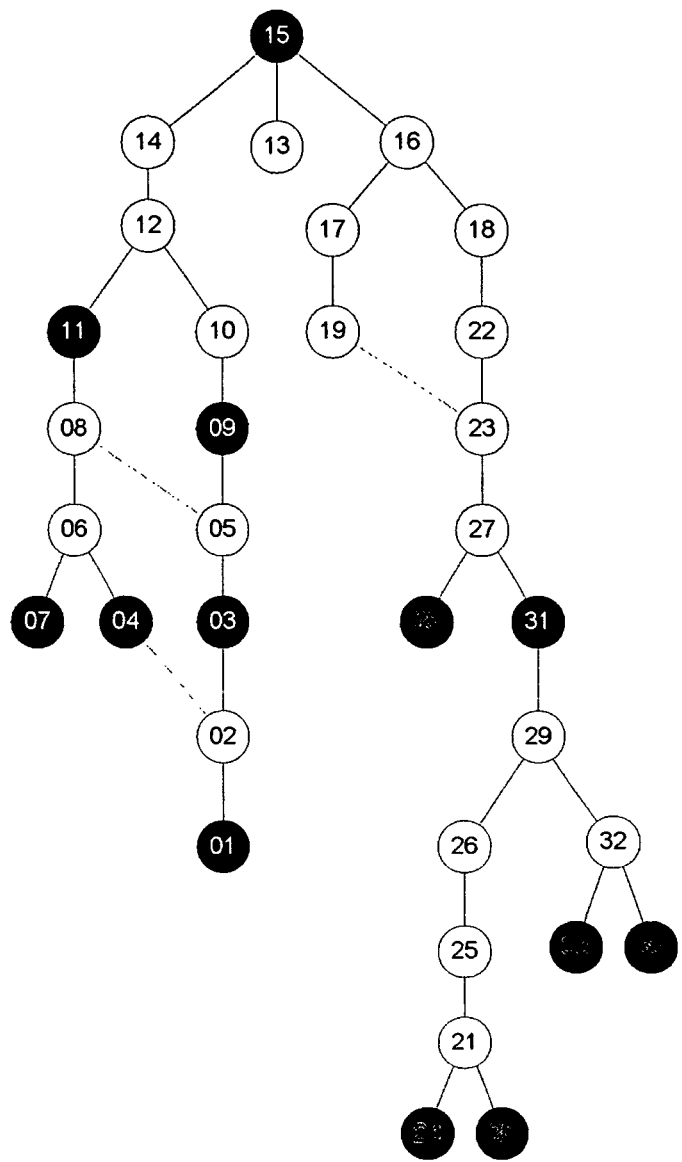
Fig 6c – An example tree representation of methotrexate molecule

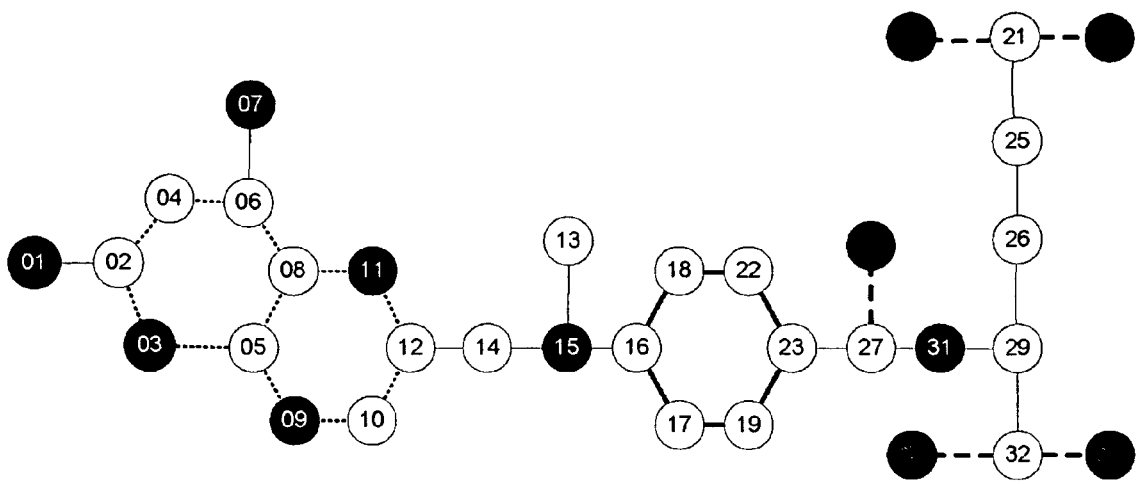
Fig 6d – An example graph representation of methotrexate molecule

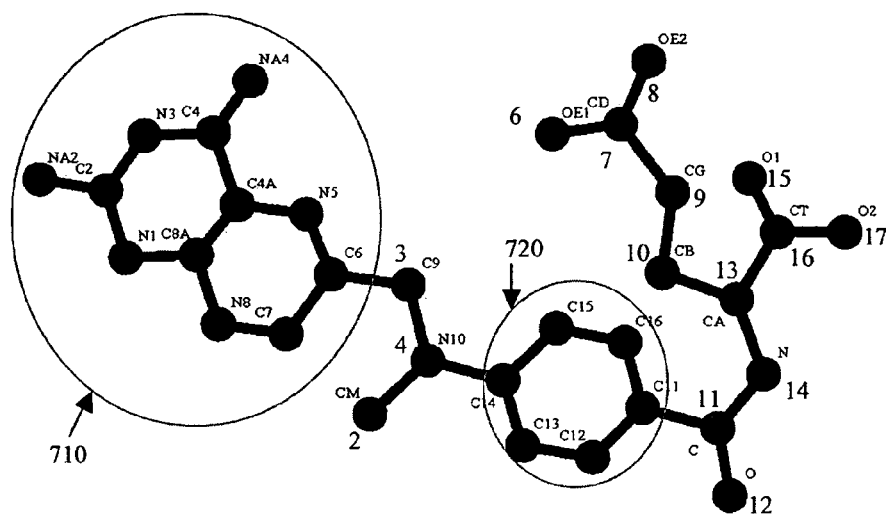
Fig 7a – A schematic of methotrexate molecule
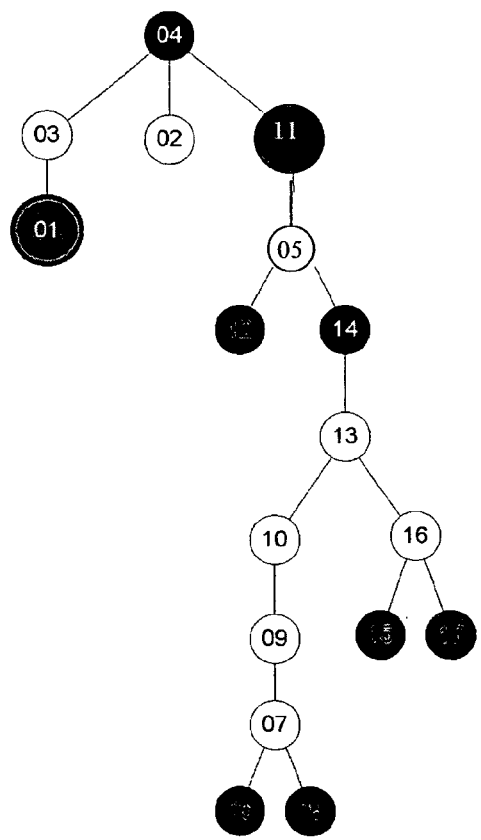
Figure 7b – An example tree representation of methotrexate molecule

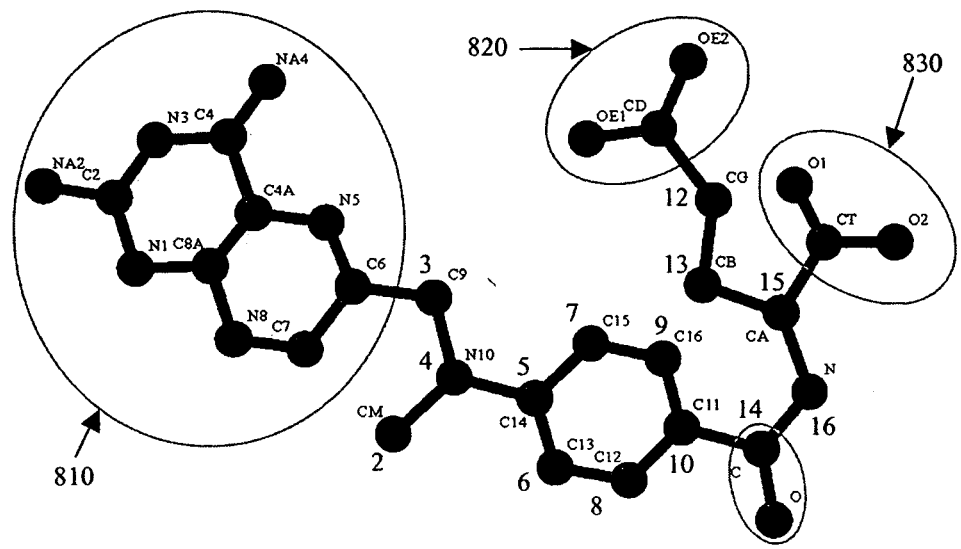
Fig 8a – Schematic of methotrexate molecule
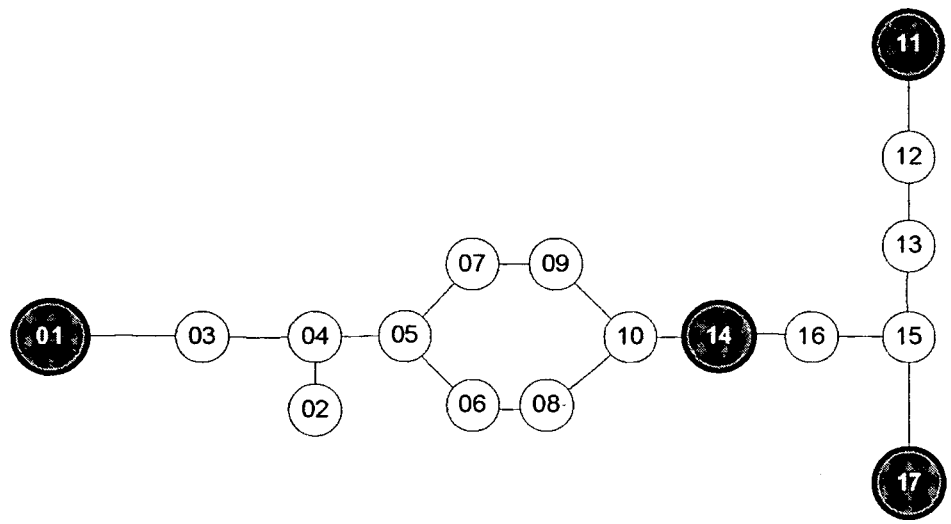
Figure 8b – An example graph representation of methotrexate molecule

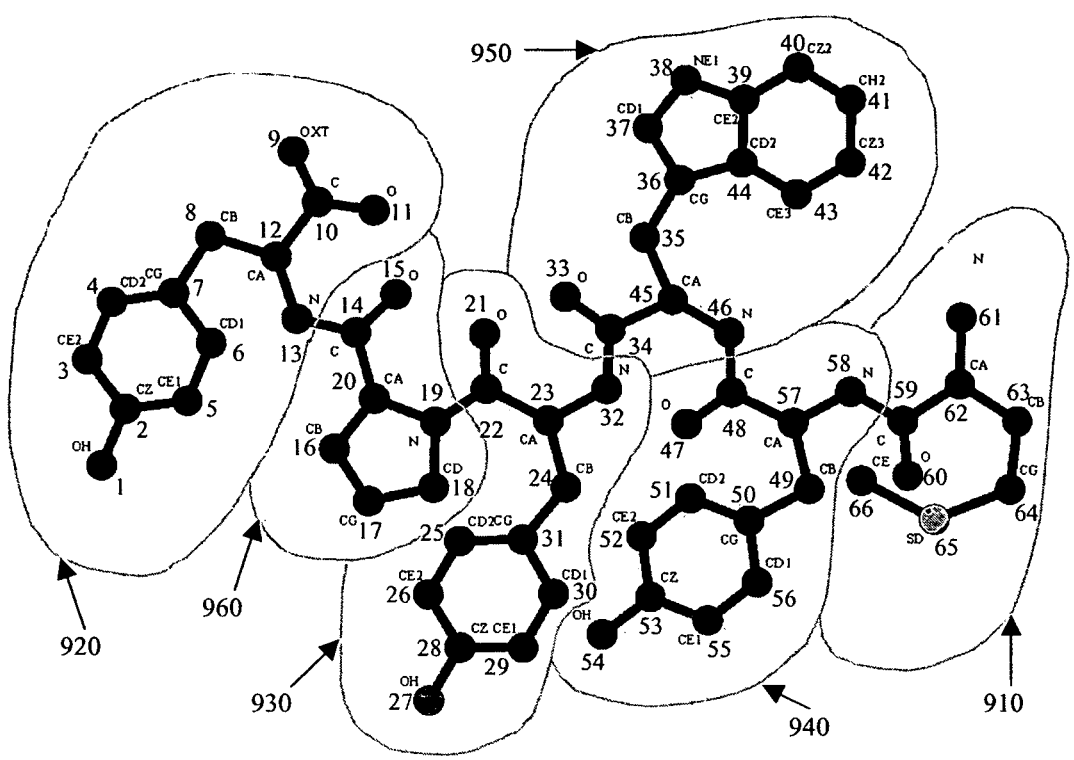
Figure 9a – Schematic of a six amino acid polypeptide MYWYPY

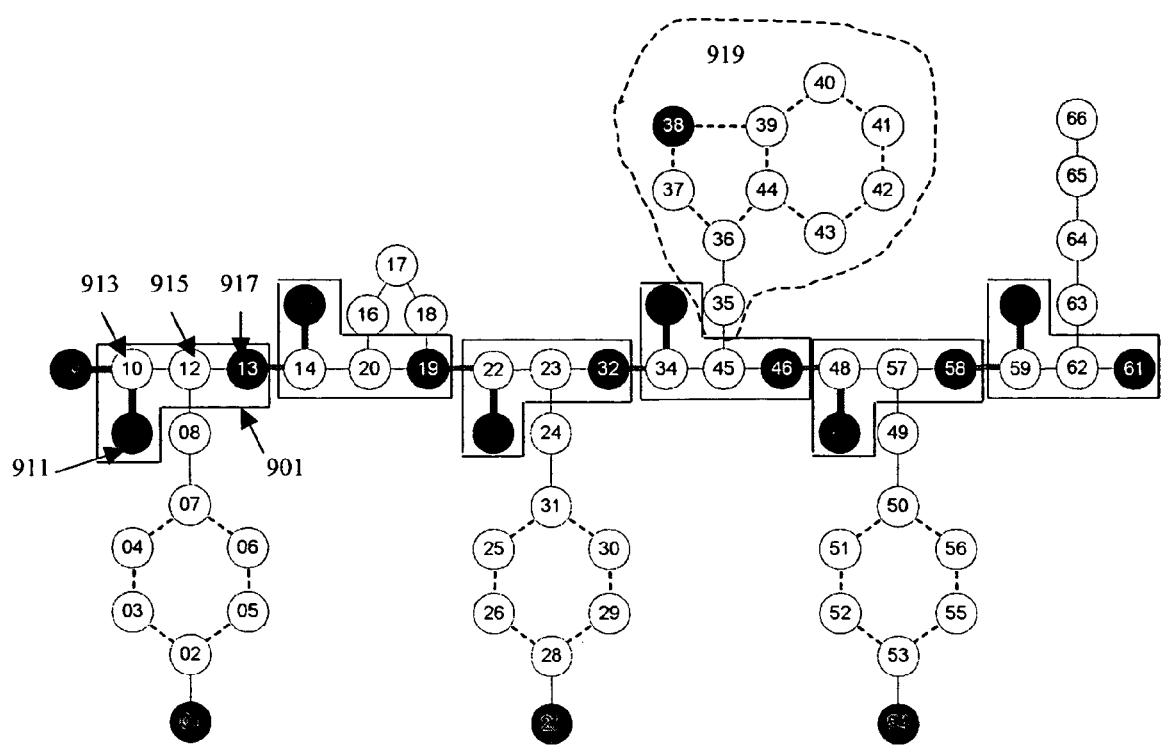
Figure 9b: Example graph representation of MYWYPY

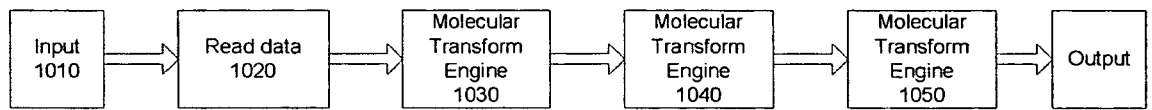
Figure 10: An example of a molecule processing pipeline

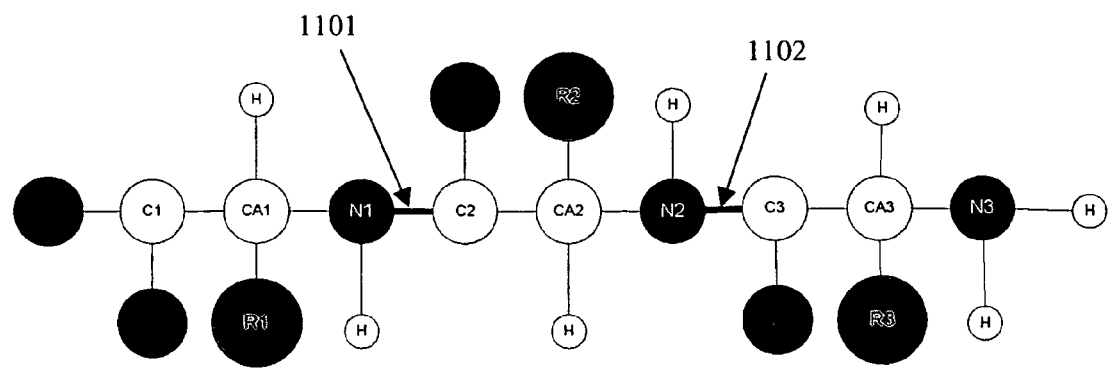
Figure 11a: Schematic of a hypothetical molecule
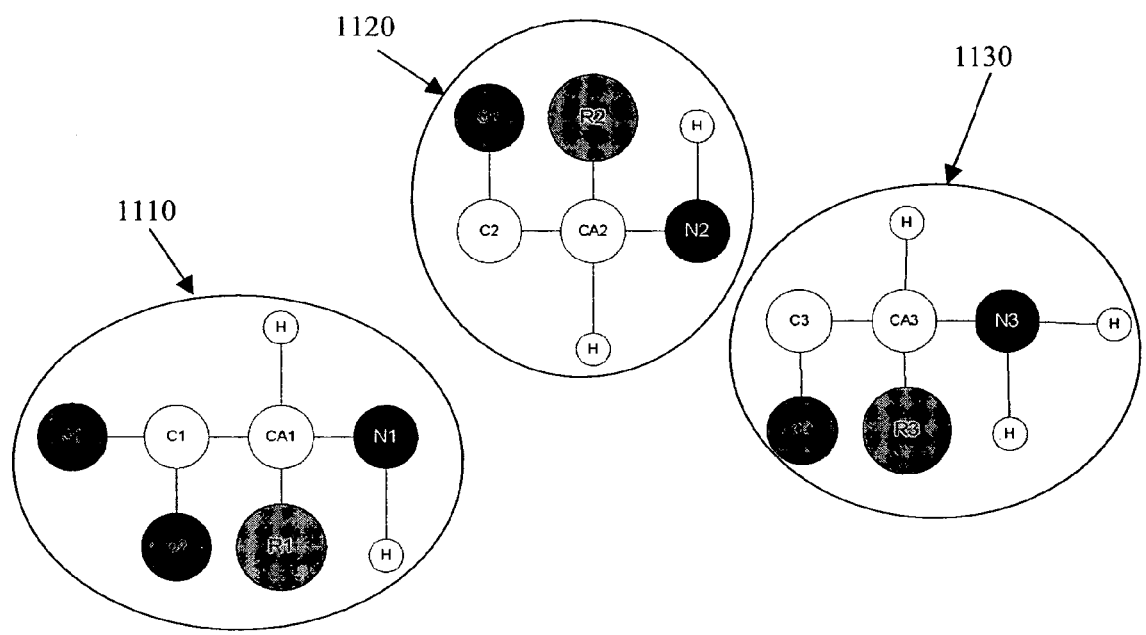
Figure 11b: Result of application of link removal operator on hypothetical molecule of figure 11a

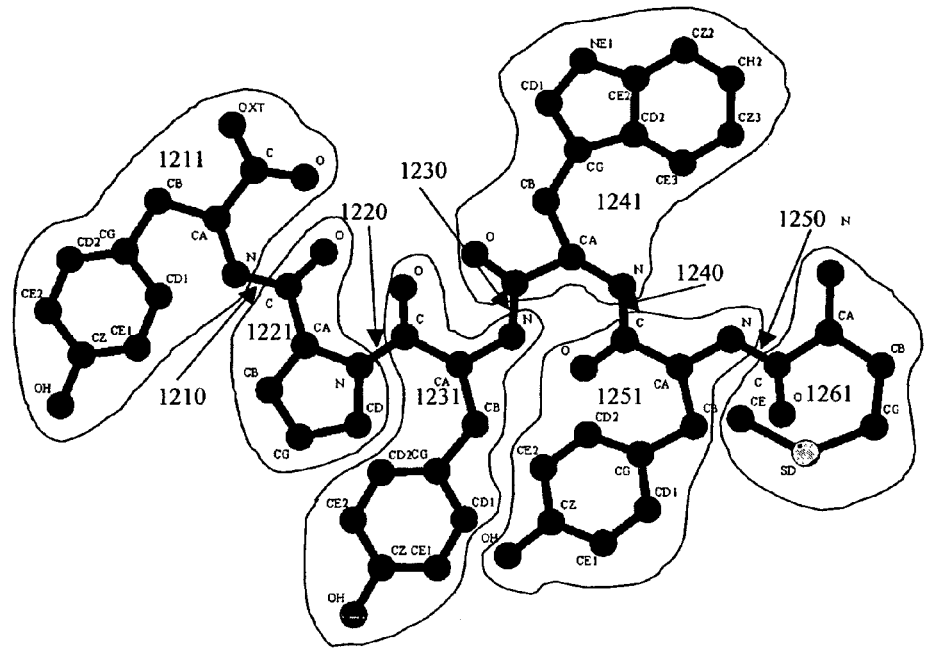
Figure 12a: Schematic of polypeptide MYWYPY, showing a result of applying link removal operator
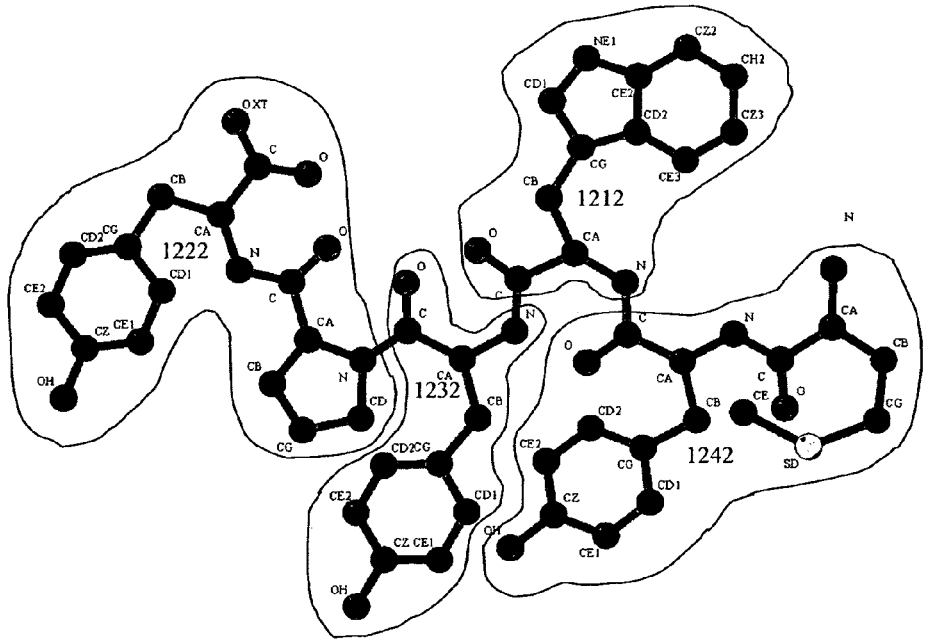
Figure 12b: Schematic of polypeptide MYWYPY, showing another result of applying link removal operator

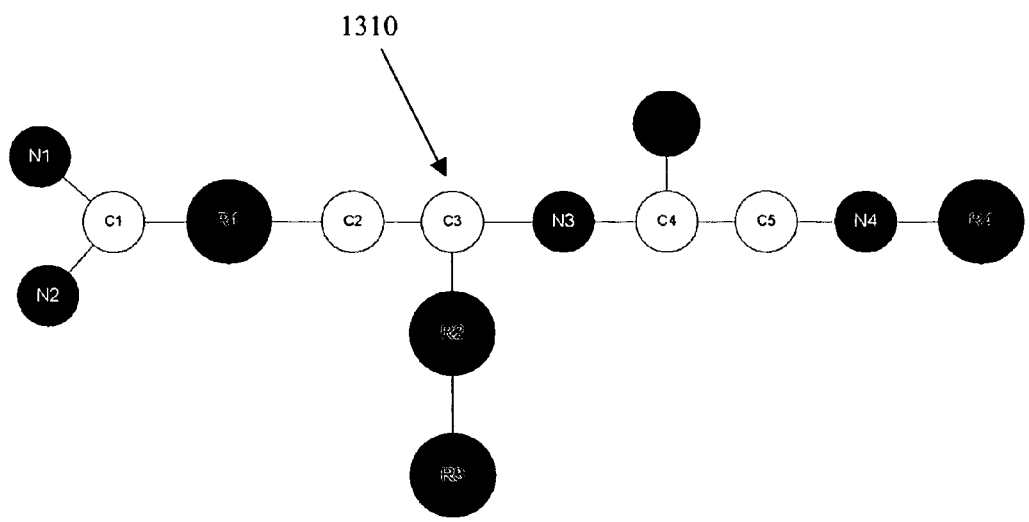
Figure 13a: Schematic of a hypothetical molecule
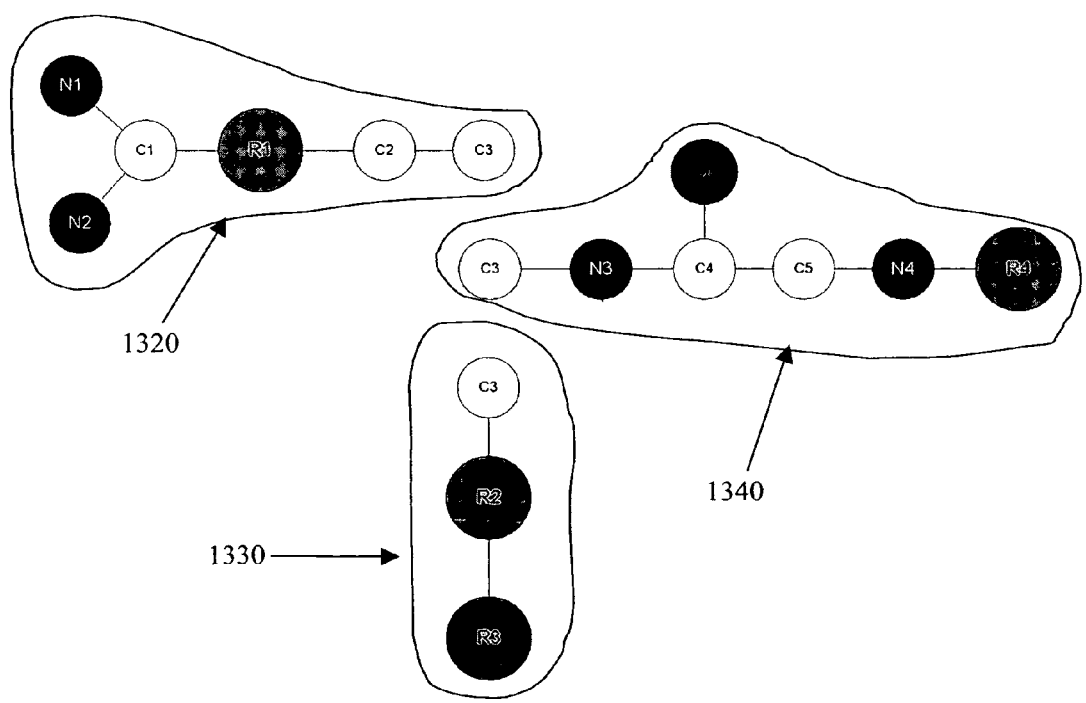
Figure 13b: An example of node cleaving on the hypothetical molecule of figure 13a

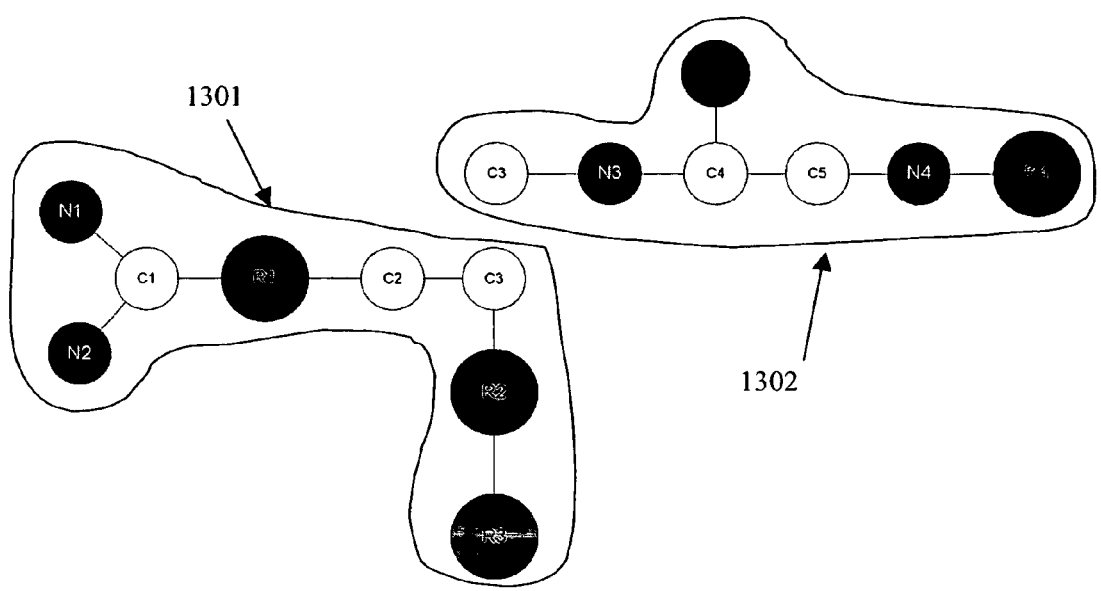
Figure 13c: Another example of node cleaving on the hypothetical molecule of figure 13a

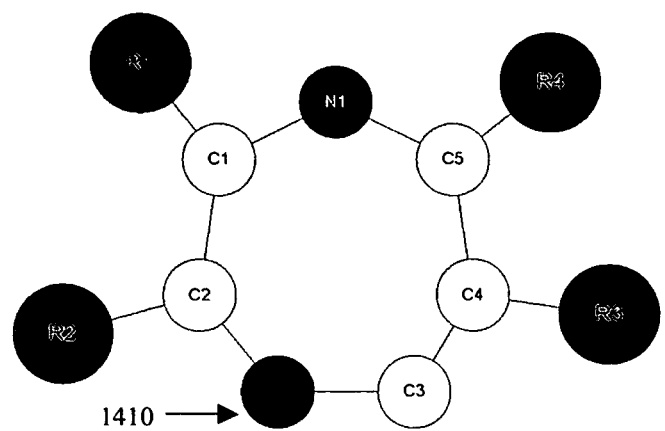
Figure 14a: Schematic of a hypothetical molecule
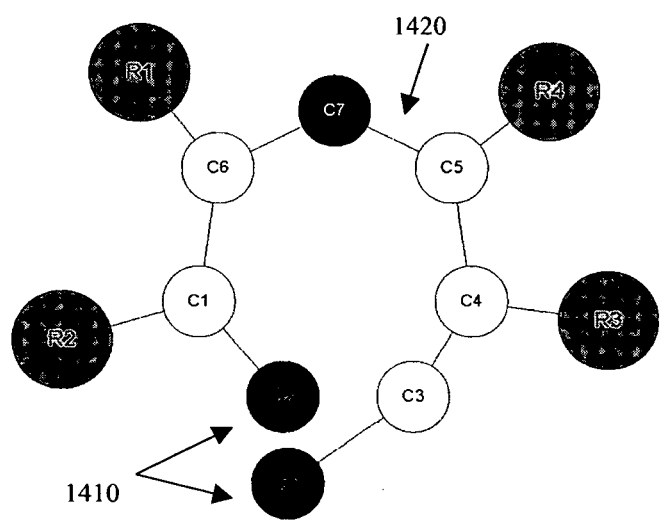
Fig 14b: An example of node cleaving on the hypothetical molecule of figure 14a

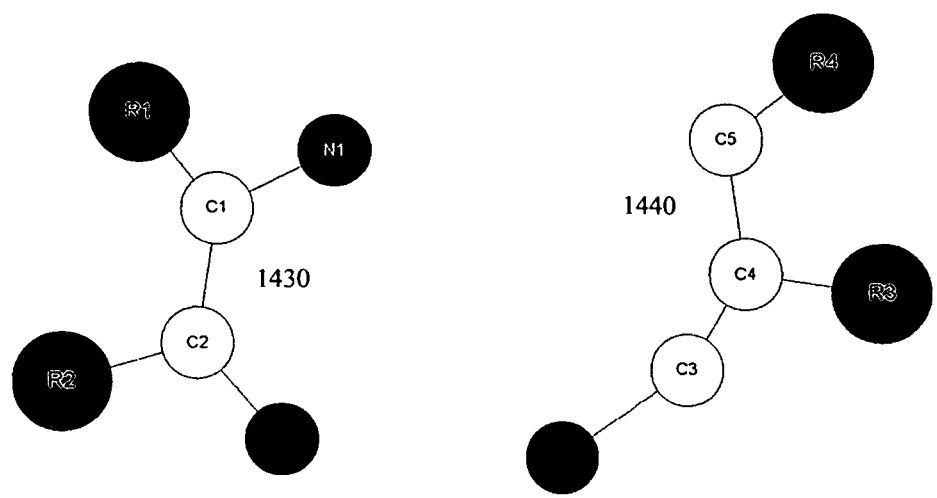
Fig 14c: An example of node cleaving on the hypothetical molecule of figure 14c

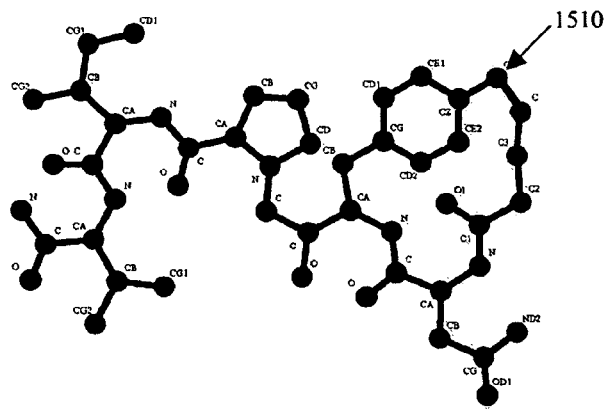
Figure 15a – Schematic of a molecule CH2-CBG-ASN-TYR-CH2-PRO-ILE-VAL-NH
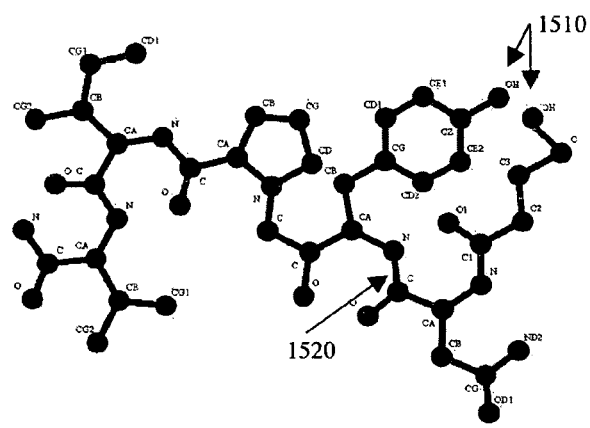
Figure 15b – Example of node cleaving for molecule CH2-CBG-ASN-TYR-CH2-PRO-ILE-VAL-NH
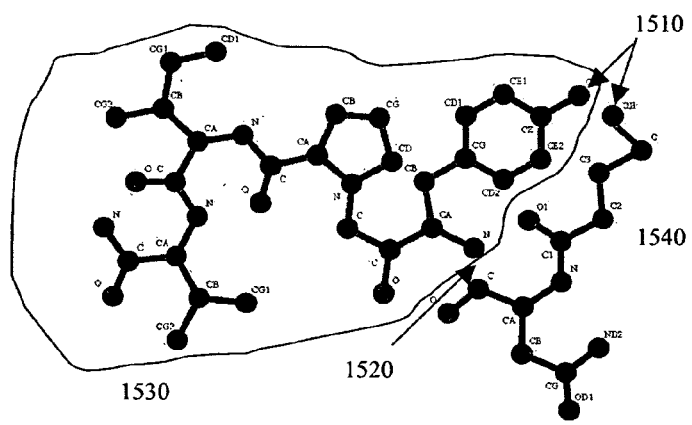
Figure 15c – Example of node cleaving for molecule CH2-CBG-ASN-TYR-CH2-PRO-ILE-VAL-NH

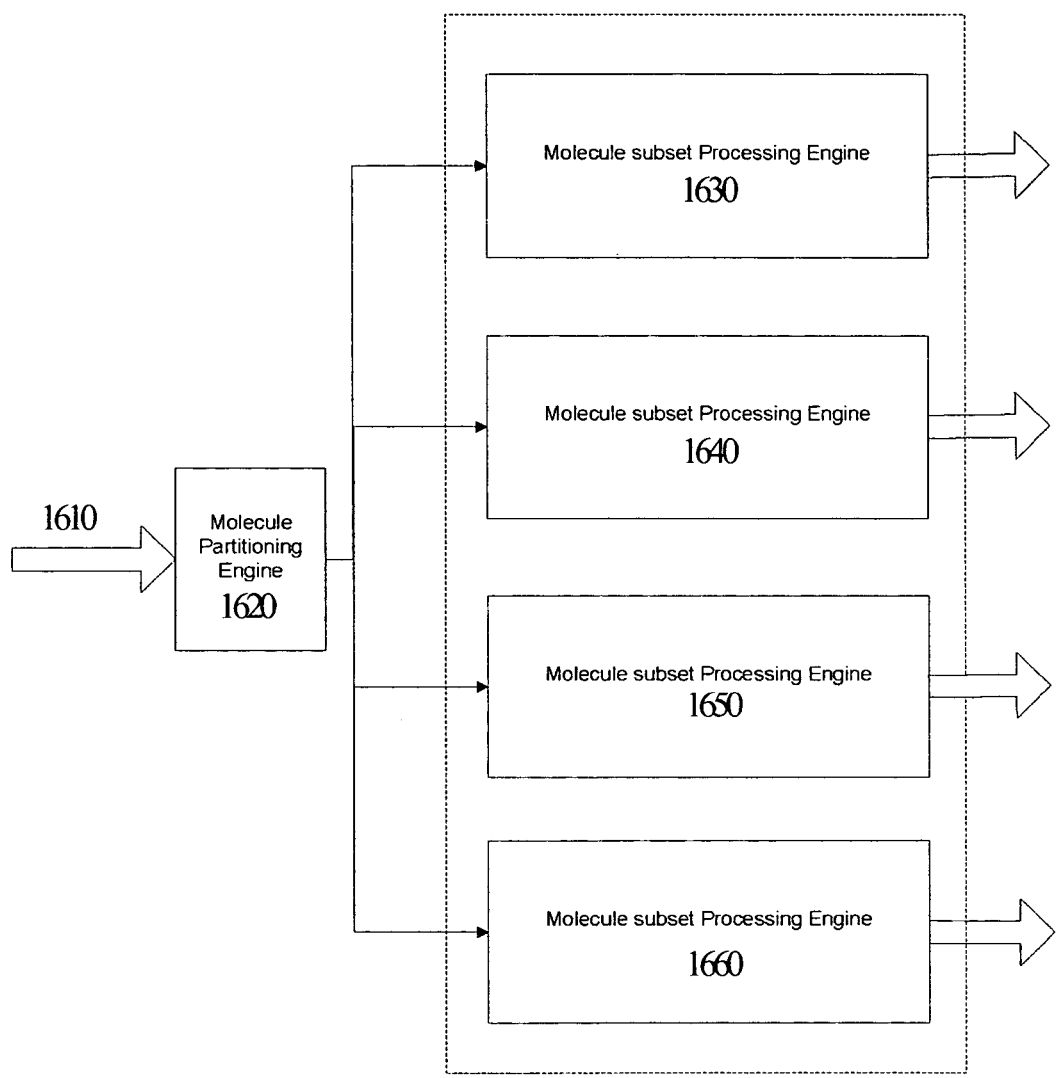
Figure 16: An example of a molecule processing pipeline

METHOD AND DEVICE FOR PARTITIONING A MOLECULE

CROSS-REFERENCES TO RELATED APPLICATIONS

The present application claims priority from and is a non provisional application of U.S. Provisional Application No. 60/511,189, entitled "METHOD AND DEVICE FOR PARTITIONING A MOLECULE" filed Oct. 14, 2003, the entire contents of which are herein incorporated by reference for all purposes.

FIELD OF THE INVENTION

The present invention generally relates to bioinformatics, proteomics, molecular modeling, computer-aided molecular design (CAMD), and more specifically computer-aided drug design (CADD) and computational modeling of molecular combinations.

BACKGROUND OF THE INVENTION

An explanation of conventional drug discovery processes and their limitations is useful for understanding the present invention.

Discovering a new drug to treat or cure some biological condition, is a lengthy and expensive process, typically taking on average 12 years and $800 million per drug, and taking possibly up to 15 years or more and $1 billion to complete in some cases. The process may include wet lab testing/experiments, various biochemical and cell-based assays, animal models, and also computational modeling in the form of computational tools in order to identify, assess, and optimize potential chemical compounds that either serve as drugs themselves or as precursors to eventual drug molecules.

A goal of a drug discovery process is to identify and characterize a chemical compound or ligand, i.e., binder, biomolecule, that affects the function of one or more other biomolecules (i.e., a drug "target") in an organism, usually a biopolymer, via a potential molecular interaction or combination. Herein the term biopolymer refers to a macromolecule that comprises one or more of a protein, nucleic acid (DNA or RNA), peptide or nucleotide sequence or any portions or fragments thereof. Herein the term biomolecule refers to a chemical entity that comprises one or more of a biopolymer, carbohydrate, hormone, or other molecule or chemical compound, either inorganic or organic, including, but not limited to, synthetic, medicinal, drug-like, or natural compounds, or any portions or fragments thereof. The target molecule is typically a disease-related target protein or nucleic acid for which it is desired to affect a change in function, structure, and/or chemical activity in order to aid in the treatment of a patient disease or other disorder. In other cases, the target is a biomolecule found in a disease-causing organism, such as a virus, bacteria, or parasite, that when affected by the drug will affect the survival or activity of the infectious organism. In yet other cases, the target is a biomolecule of a defective or harmful cell such as a cancer cell. In yet other cases, the target is an antigen or other environmental chemical agent that may induce an allergic reaction or other undesired immunological or biological response.

The target molecule is typically a disease-related target protein or nucleic acid for which it is desired to affect a change in function, structure, and/or chemical activity in order to aid in the treatment of a patient disease or other disorder. In other cases, the target is a biomolecule found in a disease-causing organism, such as a virus, bacteria, or parasite, that when affected by the drug will affect the survival or activity of the infectious organism. In yet other cases, the target is a biomolecule of a defective or harmful cell such as a cancer cell. In yet other cases the target is an antigen or other environmental chemical agent that may induce an allergic reaction or other undesired immunological or biological response.

The ligand is typically what is known as a small molecule drug or chemical compound with desired drug-like properties in terms of potency, low toxicity, membrane permeability, solubility, chemical/metabolic stability, etc. In other cases, the ligand may be biologic such as an injected protein-based or peptide-based drug or even another full-fledged protein. In yet other cases the ligand may be a chemical substrate of a target enzyme. The ligand may even be covalently bound to the target or may in fact be a portion of the protein, e.g., protein secondary structure component, protein domain containing or near an active site, protein subunit of an appropriate protein quaternary structure, etc.

Throughout the remainder of the background discussion, unless otherwise specifically differentiated, a (potential) molecular combination will feature one ligand and one target, the ligand and target will be separate chemical entities, and the ligand will be assumed to be a chemical compound while the target will be typically a biological protein (mutant or wild type). Note that the frequency of nucleic acids (both DNA/RNA) as targets will likely increase in coming years as advances in gene therapy and pathogenic microbiology progress. Also the term "molecular complex" will refer to the bound state between the target and ligand when interacting with one another in the midst of a suitable (often aqueous) environment. A "potential" molecular complex refers to a bound state that may occur albeit with low probability and therefore may or may not actually form under normal conditions.

The drug discovery process itself typically includes four different subprocesses: (1) target validation; (2) lead generation/optimization; (3) preclinical testing; and (4) clinical trials and approval.

Target validation includes determination of one or more targets that have disease relevance and usually takes two-and-a-half years to complete. Results of the target validation phase might include a determination that the presence or action of the target molecule in an organism causes or influences some effect that initiates, exacerbates, or contributes to a disease for which a cure or treatment is sought. In some cases a natural binder or substrate for the target may also be determined via experimental methods.

Lead generation typically involves the identification of lead compounds that can bind to the target molecule and thereby alter the effects of the target through either activation, deactivation, catalysis, or inhibition of the function of the target, in which case the lead would be a viewed as a suitable candidate ligand to be used in the drug application process. Lead optimization involves the chemical and structural refinement of lead candidates into drug precursors in order to improve binding affinity to the desired target, increase selectivity, and also to address basic issues of toxicity, solubility, and metabolism. Together lead generation and lead optimization typically takes about three years to complete and might result in one or more chemically distinct leads for further consideration.

In preclinical testing, biochemical assays and animal models are used to test the selected leads for various pharmacokinetic factors related to drug absorption, distribution, metabolism, excretion, toxicity, side effects, and required dosages. This preclinical testing takes approximately one year. After the preclinical testing period, clinical trials and approval take another six to eight or more years during which the drug candidates are tested on human subjects for safety and efficacy.

Rational drug design generally uses structural information about drug targets (structure-based) and/or their natural ligands (ligand-based) as a basis for the design of effective lead candidate generation and optimization. Structure-based rational drug design generally utilizes a three-dimensional model of the structure for the target. For target proteins or nucleic acids such structures may be as the result of X-ray crystallography/NMR or other measurement procedures or may result from homology modeling, analysis of protein motifs and conserved domains, and/or computational modeling of protein folding or the nucleic acid equivalent. Model-built structures are often all that is available when considering many membrane-associated target proteins, e.g., GPCRs and ion channels. The structure of a ligand may be generated in a similar manner or may instead be constructed ab initio from a known 2-D chemical representation using fundamental physics and chemistry principles, provided the ligand is not a biopolymer.

Rational drug design may incorporate the use of any of a number of computational components ranging from computational modeling of target-ligand molecular interactions and combinations to lead optimization to computational prediction of desired drug-like biological properties. The use of computational modeling in the context of rational drug design has been largely motivated by a desire to both reduce the required time and to improve the focus and efficiency of drug research and development, by avoiding often time consuming and costly efforts in biological "wet" lab testing and the like.

Computational modeling of target-ligand molecular combinations in the context of lead generation may involve the large-scale in-silico screening of compound libraries (i.e., library screening), whether the libraries are virtually generated and stored as one or more compound structural databases or constructed via combinatorial chemistry and organic synthesis, using computational methods to rank a selected subset of ligands based on computational prediction of bioactivity (or an equivalent measure) with respect to the intended target molecule.

Throughout the text, the term "binding mode" refers to the 3-D molecular structure of a potential molecular complex in a bound state at or near a minimum of the binding energy (i.e., maximum of the binding affinity), where the term 'binding energy' (sometimes interchanged with 'binding free energy' or with its conceptually antipodal counterpart 'binding affinity') refers to the change in free energy of a molecular system upon formation of a potential molecular complex, i.e., the transition from an unbound to a (potential) bound state for the ligand and target.

Binding affinity is of direct interest to drug discovery and rational drug design because the interaction of two molecules, such as a protein that is part of a biological process or pathway and a drug candidate sought for targeting a modification of the biological process or pathway, often helps indicate how well the drug candidate will serve its purpose. Furthermore, where the binding mode is determinable, the action of the drug on the target can be better understood. Such understanding may be useful when, for example, it is desirable to further modify one or more characteristics of the ligand so as to improve its potency (with respect to the target), binding specificity (with respect to other target biopolymers), or other chemical and metabolic properties.

A number of laboratory methods exist for measuring or estimating affinity between a target molecule and a ligand. Often the target might be first isolated and then mixed with the ligand in vitro and the molecular interaction assessed experimentally such as in the myriad biochemical and functional assays associated with high throughput screening. However, such methods are most useful where the target is simple to isolate, the ligand is simple to manufacture and the molecular interaction easily measured, but is more problematic when the target cannot be easily isolated, isolation interferes with the biological process or disease pathway, the ligand is difficult to synthesize in sufficient quantity, or where the particular target or ligand is not well characterized ahead of time. In the latter case, many thousands or millions of experiments might be needed for all possible combinations of the target and ligands, making the use of laboratory methods unfeasible.

While a number of attempts have been made to resolve this bottleneck by first using specialized knowledge of various chemical and biological properties of the target (or even related targets such as protein family members) and/or one or more already known natural binders or substrates to the target, to reduce the number of combinations required for lab processing, this is still impractical and too expensive in most cases. Instead of actually combining molecules in a laboratory setting and measuring experimental results, another approach is to use computers to simulate or characterize molecular interactions between two or more molecules (i.e., molecular combinations modeled in silico). The use of computational methods to assess molecular combinations and interactions is usually associated with one or more stages of rational drug design, whether structure-based, ligand-based, or both.

When computationally modeling the nature and/or likelihood of a potential molecular combination for a given target-ligand pair, the actual computational prediction of binding mode and affinity is customarily accomplished in two parts: (a) "docking", in which the computational system attempts to predict the optimal binding mode for the ligand and the target and (b) "scoring", in which the computational system attempts to estimate the binding affinity associated with the computed binding mode. During library screening, scoring may also be used to predict a relative binding affinity for one ligand vs. another ligand with respect to the target molecule and thereby rank prioritize the ligands or assign a probability for binding.

Docking may involve a search or function optimization algorithm, whether deterministic or stochastic in nature, with the intent to find one or more system poses that have favorable affinity. Scoring may involve more refined estimation of an affinity function, where the affinity is represented in terms of a combination of one or more empirical, molecular-mechanics-based, quantum mechanics-based, or knowledge-based expressions, i.e., a scoring function. Individuals scoring functions may themselves be combined to form a more robust consensus-scoring scheme using a variety of formulations. In practice there are many different docking strategies and scoring schemes employed in the context of today's computational drug design.

Whatever the choice of computational method there are inherent trade-offs between the computational complexity of both the underlying molecular models and the intrinsic numerical algorithms, and the amount of computing resources (time, number of CPUs, number of simulations) that must be allocated to process each molecular combination. For example, while highly sophisticated molecular dynamics simulations (MD) of the two molecules surrounded by explicit water molecules and evolved over trillions of time steps may lead to higher accuracy in modeling the potential molecular combination, the resultant computational cost (i.e., time and computing power) is so enormous that such simulations are intractable for use with more than just a few molecular combinations. On the other hand, the use of more primitive models for representing molecular interactions, in conjunction with multiple, and often error-prone, modeling shortcuts and approximations, may result in more acceptable computational cost but will invariably cause significant performance degradation in terms of modeling accuracy and predictive power. Currently, even the process of checking a library of drug candidates against a target protein takes too long for the required accuracy using current computational systems.

Trade-offs between accuracy and speed also exist for other computational steps in rational drug design. For example, large virtual libraries need to be clustered both accurately and rapidly into groups of similar molecules for fast virtual screening. In another example, lead refinement requires searching a molecule library accurately and rapidly for molecules similar to ones judged to have docked well in the lead generation stage. Current techniques for library screening and searching are so inaccurate and inefficient that they are not viable as part of a rational drug discovery solution.

This invention is generally concerned with providing a method to generate molecular representations in a manner to enable efficient molecular processing in a variety of scenarios. Nearly all computational processes involved in rational drug design and discovery—library construction, molecular matching, library search, docking, scoring—can benefit from a method to process molecular representations efficiently. Here processing molecular representation may mean transforming the structure of the molecules or parts of molecules by rotating bonds, lengthening or contracting bonds, rotating groups of atoms, etc. It may also involve calculating affinity functions between molecules or parts of molecules. Because of the wide variety of potential inputs—tens of millions of molecules of different sizes and structures—and many different types of molecular processing, demands on a computational system's resources can vary widely. For example, it typically takes less computational resources to calculate the binding affinity for a smaller molecule than for a larger molecule, against the same target. In another example, it is generally computationally cheaper to calculate spatial transformations for a smaller molecule than a large molecule.

It is generally understood by those skilled in the art that variable computational cost tasks tend to be inefficient whether in software executing on a general purpose microprocessor, or in specially designed hardware. When implemented as software, the unpredictability of computational cost for a task can result in poor code locality and poor data locality, can result in unpredictable memory accesses (for example, when page faults occur), and limits how much the software can be optimized, which can severely constrain the software's applications. When a variable computational cost task is implemented in specially designed hardware, it greatly increases the complexity of hardware design, leading to longer and costlier design process and the final design tends to be much less efficient than for constant cost tasks. Therefore it is advantageous that a variable cost task be implemented as a collection of one or more constant cost tasks.

FIG. 1 shows an example of a general processing system 100, which consists of a series of processing engines 101, 102, 103, 104 such that the output of each processing engine is the input of the following processing engine. The input 110 for the first engine 101 is from an input block, which may be a database server in one embodiment, a file server in another embodiment, and storage on a system board for yet another embodiment. The output of the final engine 104 goes to an output block 120, which may be a database server in one embodiment, storage on the processor in another embodiment, and storage on the system board in another embodiment. Such a series of engines 100 is also known as a pipeline.

The amount of time taken by a pipeline stage to produce output from its input is defined as a pipeline stage interval (or, stage interval). Input to the pipeline stage is read at the start of the stage interval; input data is guaranteed to be available for reading once the stage interval starts, not before. Output from the pipeline stage is guaranteed to be available only after the end of the stage interval, not before.

It should be evident that processing engines 101, 102, 103, and 104 are never idle if the stage interval for each processing engine is of exactly the same duration, i.e., if each stage is performing a constant cost task. The next input is available for processing as soon as a particular processing engine has produced output from an input; no time is spent idle by the engine waiting for the next input. If one or more of the engines take longer than other engines in the pipeline to produce their output, some of the engines spend some time sitting idle, thus making for less than 100% utilization of idling processing engines. Processor engine utilization can be improved by reducing the time taken by slower engines to match the time taken by faster engines. In one example, stage interval for each engine 101, 103, 104, is 10 cycles, and the stage interval for 102 is 20 cycles. Here a cycle means the fundamental period of time recognized by a computer, generally determined by the system clock rate. In the current example, engines 101, 103, and 104 will be idle for 10 out of every 20 cycles resulting in only a 50% utilization of three out of four engines in the pipeline. In one example, decreasing the stage interval for 102 to 15 cycles improves utilization of 101, 103, and 104 to 66.7%. In another example, decreasing the stage interval for 102 to 10 cycles improves utilization of 101, 103, and 104 to 100%. Further decreasing the stage interval for 102 to 5 cycles improves utilization of 101, 103, and 104 to 100% but decreases utilization of 102 to 50%. Thus utilization of engines in the pipeline can be improved by designing the engines and their input data such that, as far as possible, each stage interval is of the same duration. Maximal engine utilization is achieved when the stage interval for all engines is of the same duration.

In one embodiment, partitioning input data into smaller sets can decrease the stage interval for an engine in the pipeline. Greater efficiency can also be obtained by partitioning the input such that the engine takes approximately the same time for each partition. In an embodiment of the pipeline, it may be desirable to make the pipeline maximally efficient by making the engine take exactly, not approximately, the same amount of time for each partition. Another method of decreasing the duration of a stage interval is to devote more computational units to the pipeline stage for doing the same amount of computational work.

A pipeline can also be made more efficient by increasing the duration of the stage interval for a stage that is faster than other stages in the pipeline. A method of increasing the stage interval duration is to devote fewer computational units to the stage for doing the same amount of computational work. Another method of increasing the duration of a stage interval is to let the engine idle for some time Recall that a wide variety of potential inputs—for example, tens of millions of molecules of different sizes and structures—can make widely varying demands on the computational system. Demands on the system may include widely varying amounts of storage, and transmission bandwidth for input data. For example, if the system processes molecules in their entirety, then a larger molecule will need more storage on the processor, than a smaller molecule. Therefore, in order to be able to process the widest variety of molecules, the processor must be able to store data associated with the largest molecule, even if many of the input molecules may be much smaller than the largest molecule. Clearly, designing storage to hold the largest molecule is inefficient and wasteful.

Storage and transmission bandwidth requirements can be reduced by partitioning input molecular data into smaller parts, such that each part can be processed in a pipelined manner. In such a case we need to transmit and store only those parts of molecular data that are being processed by the pipeline at any given time, thus obviating the need to transmit and store the entire molecule. Additionally, the size of molecule that the engine can process is no longer determined by the size of storage on the processor or the system board. The processing engine is able to process molecules of any size—small or large—as long as they are partitioned into smaller parts.

We have discussed how pipelined processing can be enabled by partitioning input data into smaller parts. The pipeline implementation itself imposes limits on the size of a partition. It will be understood by those skilled in the arts that if the partition size is very small, then greater number of pipeline stages are needed to perform the desired computations. The stage interval for each pipeline stage will be very short because each stage needs to process very small amount of data. But the increased number of pipeline stages implies more complexity in the design of the pipeline. Increased complexity in the pipeline can be due to various reasons, for example, the increased amount of routing between pipeline stages, possible increased amount of storage between pipeline stages, etc. Increased complexity generally results in a costlier and longer design cycle, and finally a more expensive product.

The invention described in this patent seeks to increase the computational efficiency of molecular processing by providing a method to partition the input, i.e., representation of a molecule, such that each partition makes approximately the same computational demands on the system. In one example, computational demand can be measured by the amount of storage on or off the processors. In another example, computational demand can be measured by the amount of bandwidth needed to transfer data to and from one or more processors. In yet another example, computational demand can be measured by the number of computational units, which in turn is measured by the number of gates, routing requirements, size of compute blocks on the processors, etc.

Current computational methods for ligand-target docking use digital representations of molecules that are designed for their particular docking method. For example, FlexX computes the binding mode of a potential drug molecule by incrementally docking fragments of the molecule. FlexX constructs its fragments by breaking all bonds in the molecule that are deemed to be flexible, thus constructing fragments that are themselves rigid. Another computational docking method, similar to FlexX, that makes use of molecular fragments is the place-and-join method [22]. Molecular fragments used in the place-and-join method are constructed by breaking the molecule at an atom that has two adjacent flexible bonds. The fragments are then 'placed' incrementally and 'joined' at the break points in an attempt to reconstruct the molecule's binding mode. Incremental docking methods create fragments that are not guaranteed to make approximately the same demand on computational resources, therefore, they are unsuitable for a docking implementation that relies on a pipelined implementation.

There also exist some molecular representation schemes that are inspired by physical or chemical properties of molecules rather than the need to speed up certain kinds of computations. RECAP partitions molecules based on a set of chemical rules [58]. RECAP rules are intended to create fragments that can be synthesized chemically. The rules do not depend on the rigidity or flexibility of resulting fragments. RECAP rules are also not intended to facilitate more efficient molecular processing computations, but for providing a guide for combinatorial drug design and synthesis.

This invention enables partitioning of molecules into smaller parts such that the parts can be stored, transmitted, and otherwise processed in specially designed hardware with greater efficiency than the entire molecule. The partitioned representation is constructed by taking into account the structure of the molecule, the processing to be performed on the molecule, and the design of the pipeline. In a preferred embodiment, first a graph representation of the molecule is constructed. The graph representation is first partitioned using an invariant link removal operator such that it produces subgraphs that satisfy certain partitioning criteria. If one or more subgraphs need further partitioning, a node-cleaving operator is applied such that it produces further subgraphs that also satisfy a set of partitioning criteria. Finally, if any subgraphs still need further partitioning, all types of links, not just invariant links, can be removed, and nodes can be cleaved until the resulting subgraphs satisfy a final set of criteria. Graph partitioning results in smaller partitions that are far more efficient to store, transmit, and process, than entire molecules. The increase in efficiency makes it possible to design and run applications which require complex molecular processing, such as rational drug discovery, virtual library design, etc.

SUMMARY OF THE INVENTION

The present invention is a method for partitioning a molecular representation into smaller parts to facilitate faster and more efficient storage, transmission, and processing of molecular subsets. The method includes providing a molecular representation that includes atoms and bonds between atoms. The molecular representation is partitioned into one or more parts based on molecular structure and the transformations that the molecular subset is expected to undergo as part of molecular processing. The partitioning process can also take into account constraints due to the device on which the partitions are to be used.

The invention is of wide usefulness in molecular processing. Partitioned molecular subsets can be used in efficient calculation of molecular transformations, affinity functions, generation of new conformations, molecular similarity calculations, etc. The increase in efficiency of such calculations makes it possible to run complex molecular processing applications, such as virtual screening.

Other features and advantages of the invention will be apparent in view of the following detailed description and preferred embodiments.

BRIEF DESCRIPTION OF THE DRAWINGS

A more complex appreciation of the invention and many of the advantages thereof will be readily obtained as the same becomes better understood by references to the detailed description when considered in connection with the accompanying drawings.

FIG. 1 is an illustration of a pipelined computational system.

FIG. 2 is an illustration of some of degrees of freedom associated with changes in molecular conformations.

FIGS. 3a, 3b, 3c and 3d show 'ball-and-stick' renderings of different conformations of a methotrexate molecule.

FIG. 4a shows an example PDB file.

FIG. 4b shows a MDL mol2 file constructed by using SYBYL to assign various chemical descriptors from the PDB file in FIG. 4a.

FIG. 4c shows a file containing physical descriptors assigned via the Amber96 force field for the molecule shown in FIGS. 4a and 4b.

FIG. 5a shows a schematic representation of the IVVL molecule.

FIG. 5b shows an example list representation of the IVVL molecule.

FIGS. 5c and 5d show two examples of tree representation of the IVVL molecule.

FIG. 6a shows a schematic of the methotrexate molecule.

FIG. 6b shows an example list representation of the methotrexate molecule.

FIG. 6c shows an example tree representation of the methotrexate molecule.

FIG. 6d shows an example graph representation of the methotrexate molecule.

FIG. 7a shows a schematic of the methotrexate molecule.

FIG. 7b shows an example tree representation of the methotrexate molecule.

FIG. 8a shows a schematic of the methotrexate molecule.

FIG. 8b shows an example graph representation of the methotrexate molecule.

FIG. 9a shows a schematic of a six amino acid polypeptide MYWYPY (SEQ ID NO:1).

FIG. 9b shows an example graph representation of molecule MYWYPY (SEQ ID NO:1).

FIG. 10 shows an example molecule processing pipeline.

FIG. 11a shows a schematic of a hypothetical molecule.

FIG. 11b shows the result of the application of a link removal operator on molecule of FIG. 11a.

FIGS. 12a and 12b show examples of link removal operator for polypeptide MYWYPY (SEQ ID NO:1).

FIG. 13a shows a schematic of a hypothetical molecule.

FIGS. 13b and 13c show examples of the application of a node-cleaving operator on the hypothetical molecule of FIG. 13a.

FIG. 14a shows a schematic of a hypothetical molecule.

FIG. 14b shows an example of node cleaving.

FIG. 14c shows an example of link removal.

FIG. 15a shows a schematic of molecule CH2-CBG-ASN-TYR-CH2-PRO-ILE-VAL-NH.

FIGS. 15b and 15c show examples of node cleaving for molecule CH2-CBG-ASN-TYR-CH2-PRO-ILE-VAL-NH.

FIG. 16 shows an example of a molecular processing pipeline.

REFERENCES AND PRIOR ART

Prior art in the field of the current invention is heavily documented.

Drews [1] provides a good overview of the current state of drug discovery. In [2] Abagyan and Totrov show the state of high throughput docking and scoring and its applications. Lamb et al. [3] further teach a general approach to the design, docking, and virtual screening of multiple combinatorial libraries against a family of proteins, finally Waskowycz et al. [4] describe the use of multiple computers to accelerate virtual screening of a large ligand library against a specific target by assigning groups of ligands to specific computers.

[1] J. Drews, "Drug Discovery: A Historical perspective", *Science*, 287, 1960-1964 (2000).

[2] Ruben Abagyan and Maxim Totrov, "High-throughput docking for lead generation", *Current Opinion in Chemical Biology*, Vol. 5, 375-382 (2001).

[3] Lamb, M. L., Burdick, K. W., Toba, S., Young, M. M., Skillman, A. G. et al., "Design, docking, and evaluation of multiple libraries against multiple targets", *Proteins*, Vol. 42, 296-318 (2001).

[4] Waszkowycz, B., Perkins, T. D. J., Sykes, R. A., Li, J., "Large-scale virtual screening for discovering leads in the post-genomic era", *IBM Systems Journal*, Vol. 40, No. 2 (2001).

There are a number of examples of software tools currently used to perform docking simulations. These methods involve a wide range of computational techniques, including use of a) rigid-body pattern-matching algorithms, either based on surface correlations, use of geometric hashing, pose clustering, or graph pattern-matching; b) fragmental-based methods, including incremental construction or 'place and join' operators; c) stochastic optimization methods including use of Monte Carlo, simulated annealing, or genetic (or memetic) algorithms; d) molecular dynamics simulations or e) hybrids strategies derived thereof.

The earliest docking software tool was a graph-based rigid-body pattern-matching algorithm called DOCK [5] [6] [7], developed at UCSF back in 1982 (v1.0) and now up to v5.0 (with extensions to include incremental construction). Other examples of graph-based pattern-matching algorithms include CLIX [8] (which in turn uses GRID [9]), FLOG [10] and LIGIN [11].

[5] Shoichet, B. K., Bodian, D. L. and Kuntz, I. D., "Molecular docking using shape descriptors", *J Comp Chem*, Vol. 13 No. 3, 380-397 (1992).

[6] Meng, E. C., Gschwend, D. A., Blaney, J. M., and I. D. Kuntz, "Orientational sampling and rigid-body minimization in molecular docking", *Proteins: Structure, Function, and Genetics*, Vol. 17, 266-278 (1993).

[7] Ewing, T. J. A. and Kuntz, I. D., "Critical Evaluation of Search Algorithms for Automated Molecular Docking and Database Screening", *J. Computational Chemistry*, Vol. 18 No. 9, 1175-1189 (1997).

[8] Lawrence, M. C. and Davis, P. C.; "CLIX: A Search Algorithm for Finding Novel Ligands Capable of Binding Proteins of Known Three-Dimensional Structure", *Proteins*, Vol. 12, 31-41 (1992).

[9] Kastenholz, M. A., Pastor, M., Cruciani, G., Haaksma, E. E. J., Fox, T., "GRID/CPCA: A new computational tool to design selective ligands", *J. Medicinal Chemistry*, Vol. 43, 3033-3044 (2000).

[10] Miller, M. D., Kearsley, S. K., Underwood, D. J. and Sheridan, R. P., "FLOG: a system to select 'quasi-flexible' ligands complementary to a receptor of known three-dimensional structure", *J. Computer-Aided Molecular Design*, Vol. 8 No. 2, 153-174 (1994).

[11] Sobolev, V., Wade, R. C., Vriend, G. and Edelman, M., "Molecular docking using surface complementarity", *Proteins*, Vol. 25, 120-129 (1996). Other rigid-body pattern-matching docking software tools include the shape-based correlation methods of FTDOCK [12] and HEX [13], the geometric hashing of Fischer et al. [14], or the pose clustering of Rarey et al. [15].

[12] Aloy, P., Moont, G., Gabb, H. A., Querol, E., Aviles, F. X., and Sternberg, M. J. E., "Modeling Protein Docking using Shape Complementarity, Electrostatics and Biochemical Information," *Proteins: Structure, Function, and Genetics*, Vol. 33, 535-549 (1998).

[13] Ritchie, D. W. and Kemp. G. J. L., "Fast Computation, Rotation, and Comparison of Low Resolution Spherical Harmonic Molecular Surfaces", *Proteins: Structure, Function, and Genetics*, Vol. 39, 178-194 (2000).

[14] Fischer, D., Norel, R., Wolfson, H. and Nussinov, R., "Surface motifs by a computer vision technique: searches, detection, and implications for protein-ligand recognition", *Proteins*, Vol. 16, 278-292 (1993).

[15] Rarey, M., Wefing, S., and Lengauer, T., "Placement of medium-sized molecular fragments into active sites of proteins", *J Computer-Aided Molecular Design*, Vol. 10, 41-54 (1996).

In general, rigid-body pattern-matching algorithms assume that both the target and ligand are rigid (i.e., not flexible) and hence may be appropriate for docking small, rigid molecules (or molecular fragments) to a simple protein with a well-defined, nearly rigid active site. Thus this class of docking tools may be suitable for de novo ligand design, combinatorial library design, or straightforward rigid-body screening of a molecule library containing multiple conformers per ligand.

Incremental construction based docking software tools include FlexX [16] [17] from Tripos (licensed from EMBL), Hammerhead [18], DOCK v4.0 [7] (as an option), and the nongreedy, backtracking algorithm of Leach et al. [19]. Programs using incremental construction in the context of de novo ligand design include LUDI [20] (from Accelrys) and GrowMol [21]. Docking software tools based on 'place and join' strategies include DesJarlais et al. [22].

[16] Kramer, B., Rarey, M. and Lengauer, T., "Evaluation of the FlexX incremental construction algorithm for protein-ligand docking", *Proteins*, Vol. 37, 228-241 (1999).

[17] Rarey, M., Kramer, B., Lengauer, T., and Klebe, G., "A Fast Flexible Docking Method Using An Incremental Construction Algorithm", *J. Mol. Biol.*, Vol. 261, 470-489 (1996).

[18] Welch, W., Ruppert, J. and Jain, A. N., "Hammerhead: Fast, fully automated docking of flexible ligands to protein binding sites", *Chemical Biology*, Vol. 3, 449-462 (1996).

[19] Leach, A. R., Kuntz, I. D., "Conformational Analysis of Flexible Ligands in Macromolecular Receptor Sites", *J. Comp. Chem.*, Vol. 13, 730-748 (1992).

[20] Bohm, H. J., "The computer program LUDI: a new method for the de novo design of enzyme inhibitors", *J. Computer-Aided Molecular Design*, Vol. 6, 61-78 (1992).

[21] Bohacek, R. S. and McMartin, C., "Multiple Highly Diverse Structures Complementary to Enzyme Binding Sites: Results of Extensive Application of a de Novo Design Method Incorporating Combinatorial Growth", *J. American Chemical Society*, Vol. 116, 5560-5571 (1994).

[22] DesJarlais, R. L., Sheridan, R. P., Dixon, J. S., Kuntz, I. D., and Venkataraghavan, R., "Docking Flexible Ligands to Macromolecular Receptors by Molecular Shape", *J. Med. Chem.*, Vol. 29, 2149-2153 (1986).

Incremental construction algorithms may be used to model docking of flexible ligands to a rigid target molecule with a well-characterized active site. They may be used when screening a library of flexible ligands against one or more targets. They are often comparatively less compute intensive, yet consequently less accurate, than many of their stochastic optimization based competitors. However, even FlexX may take on order of <1-2 minutes to process one target-ligand combination and thus may still be computationally onerous depending on the size of the library (e.g., tens of millions or more compounds). Incremental construction algorithms often employ one or more scoring functions to evaluate and rank different system poses encountered during computations. Recently FlexX was extended to FlexE [23] to attempt to account for partial flexibility of the target molecule's active site via use of user-defined ensembles of certain active site rotamers.

[23] Claussen, H., Buning, C., Rarey, M., and Lengauer, T., "FlexE: Efficient Molecular Docking Considering Protein Structure Variations", *J. Molecular Biology*, Vol. 308, 377-395 (2001).

Computational docking software tools based on stochastic optimization include ICM [24] (from MolSoft), GLIDE [25] (from Schrodinger), and LigandFit [26] (from Accelrys), all based on modified Monte Carlo techniques, and AutoDock v.2.5 [27] (from Scripps Institute) based on simulated annealing. Others based on genetic or memetic algorithms include GOLD [28] [29], DARWIN [30], and AutoDock v.3.0 [31] (also from Scripps).

[24] Abagyan, R. A., Totrov, M. M., and Kuznetsov, D. N., "Biased probability Monte Carlo conformational searches and electrostatic calculations for peptides and proteins", *J. Comp. Chem.*, Vol. 15, 488-506 (1994).

[25] Halgren, T. A., Murphy, R. B., Friesner, R. A., Beard, H. S., Frye, L. L., Pollard, W. T., and Banks, J. L., "Glide: a new approach for rapid, accurate docking and scoring. 2. Enrichment factors in database screening", *J Med. Chem.*, Vol. 47 No. 7, 1750-1759, (2004).

[26] Luty, B. A., Wasserman, Z. R., Stouten, P. F. W., Hodge, C. N., Zacharias, M., and McCammon, J. A., "Molecular Mechanics/Grid Method for the Evaluation of Ligand-Receptor Interactions", *J. Comp. Chem.*, Vol. 16, 454-464 (1995).

[27] Goodsell, D. S. and Olson, A. J., "Automated Docking of Substrates to Proteins by Simulated Annealing", *Proteins: Structure, Function, and Genetics*, Vol. 8, 195-202 (1990).

[28] Jones, G., Willett, P. and Glen, R. C., "Molecular Recognition of Receptor Sites using a Genetic Algorithm with a Description of Desolvation", *J. Mol. Biol.*, Vol. 245, 43-53 (1995).

[29] Jones, G., Willett, P., Glen, R. C., Leach, A., and Taylor, R., "Development and Validation of a Genetic Algorithm for Flexible Docking", *J. Mol. Biol.*, Vol. 267, 727-748 (1997).

[30] Taylor, J. S. and Burnett, R. M., *Proteins*, Vol. 41, 173-191 (2000).

[31] Morris, G. M., Goodsell, D. S., Halliday, R. S., Huey, R., Hart, W. E., Belew, R. K. and Olson, A. J., "Automated Docking Using a Lamarckian Genetic Algorithm and an Empirical Binding Free Energy Function", *J. Comp. Chem.*, Vol. 19, 1639-1662 (1998).

Stochastic optimization-based methods may be used to model docking of flexible ligands to a target molecule. They generally use a molecular-mechanics-based formulation of the affinity function and employ various strategies to search for one or more favorable system energy minima. They are often more compute intensive, yet also more robust, than their incremental construction competitors. As they are stochastic in nature, different runs or simulations may often result in different predictions. Traditionally most docking software tools using stochastic optimization assume the target to be nearly rigid (i.e., hydrogen bond donor and acceptor groups in the active site may rotate), since otherwise the combinatorial complexity increases rapidly making the problem difficult to robustly solve in reasonable time.

Molecular dynamics simulations have also been used in the context of computational modeling of target-ligand combinations. This includes the implementations presented in Di Nola et al. [32] and Luty et al. [16] (along with Monte Carlo). In principle, molecular dynamics simulations may be able to model protein flexibility to an arbitrary degree. On the other hand, they may also require evaluation of many fine-grained, time steps and are thus often very time-consuming (one order of hours or even days per target-ligand combination). They also often require user interaction for selection of valid trajectories. Use of molecular dynamics simulations in lead discovery is therefore more suited to local minimization of predicted complexes featuring a small number of promising lead candidates.

[32] Di Nola, A., Berendsen, H. J. C., and Roccatano, D., "Molecular Dynamics Simulation of the Docking of Substrates to Proteins", *Proteins*, Vol. 19, 174-182 (1994).

Hybrid methods may involve use of rigid-body pattern matching techniques for fast screening of selected low-energy ligand conformations, followed by Monte Carlo torsional optimization of surviving poses, and finally even molecular dynamics refinement of a few choice ligand structures in combination with a (potentially) flexible protein active site. An example of this type of docking software strategy is Wang et al. [33].

[33] Wang, J., Kollman, P. A. and Kuntz, I. D., *Proteins*, Vol. 36, 1-19 (1999). There are a number of examples of scoring functions implemented in software and used to estimate target-ligand affinity, rank prioritize different ligands as per a library screen, or rank intermediate docking poses in order to predict binding modes. Scoring functions traditionally fall into three distinct categories: a) empirical scoring functions, b) molecular-mechanics-based expressions, or (c) knowledge-based scoring functions or hybrid schemes derived thereof.

Empirically derived scoring functions (as applied to target-ligand combinations) were first inspired by the linear free-energy relationships often utilized in QSAR studies. An early example is that of Böhm et al. [20] [34] (used in LUDI). Other empirical scoring functions include SCORE [35] (used in FlexX), ChemScore [36], PLP [37], Fresno [38], and GlideScore v.2.0+ [39] (modified form of ChemScore, used by GLIDE).

[34] Böhm, H. J., "The Development of a simple empirical scoring function to estimate the binding constant for a protein-ligand complex of known three-dimensional structure", *J. Comput-Aided Mol. Des.*, Vol. 8, 243-256 (1994).

[35] Wang, R., Gao, Y. and Lai, L., "A new empirical method for estimating the binding affinity of a protein-ligand complex.", *J. Molecular Modeling*, Vol. 4, 379 (1998).

[36] Eldridge, M. D., Murray, C. W., Auton, T. R., Paolini, G. V., and Mee, R. P., "Empirical scoring functions: I. The development of a fast empirical scoring function to estimate the binding affinity of ligands in receptor complexes", *J. Computer-Aided Molecular Design*, Vol. 11, 425-445 (1997).

[37] Gelhaar, D. K., Bouzida, D.; Rejto, P. A., In "*Rational Drug Design: Novel Methodology and Practical Applications*", Parrill, L., Reddy, M. R., Ed.; American Chemical Society: Washington, D.C., pp. 292-311 (1999).

[38] Rognan D., Lauemoller S. L., Holm A., Buus S., Schinke V., *J. Medicinal Chemistry*, Vol. 42, 4650-4658 (1999).

[39] Halgren, T. A., Murphy, R. B., Friesner, R. A., Beard, H. S., Frye, L. L., Pollard, W. T., and Banks, J. L., "Glide: a new approach for rapid, accurate docking and scoring. 2. Enrichment factors in database screening", *J Med. Chem.*, Vol. 47 No. 7, 1750-1759, (2004).

In general, empirical scoring functions comprise the bulk of scoring functions used today, especially in the context of large compound library screening. The basic premise is to calibrate a linear combination of empirical energy models, each multiplied by an associated numerical weight and each representing one of a set of interaction components represented in a (so-called) 'master scoring equation', where said equation attempts to well approximate the binding free energy of a molecular combination. The numerical weight factors may be obtained by fitting to experimental binding free energy data composed for a training set of target-ligand complexes.

Molecular-mechanics-based scoring functions were first developed for use in molecular modeling in the context of molecular mechanics force fields like AMBER [40] [41], OPLS [42], MMFF [43], and CHARMM [44]. Examples of molecular-mechanics-based scoring functions include both the chemical and energy-based scoring functions of DOCK v.4.0 (based on AMBER) [7], the objective functions used in GOLD [28] [29], AutoDock v.3.0 [31] (with empirical weights), and FLOG [10].

[40] Pearlman, D. A., Case, D. A., Caldwell, J. C., Ross, W. S., Cheatham III, T. E., Ferguson, D. M., Seibel, G. L., Singh, U. C., Weiner, P., Kollman, P. A. *AMBER* 4.1, University of California, San Francisco (1995).

[41] Cornell, W. D., Cieplak, P., Bayly, C. I., Goulg, I. R., Merz, K. M., Ferguson, D. M., Spellmeyer, D. C., Fox, T., Caldwell, J. W., Kollman, P. A., "A second-generation force field for the simulation of proteins, nucleic acids, and organic molecules", *J. American Chemical Society*, Vol. 117, 5179-5197 (1995).

[42] Jorgensen, W. L., & Tirado-Rives, J., *J. American Chemical Society*, Vol. 110, 1657-1666 (1988).

[43] Halgren, T. A., "Merck Molecular Force Field. I. Basis, Form, Scope, Parameterization, and Performance of MMFF94", *J. Comp. Chem.*, Vol. 17, 490-519 (1996).

[44] Brooks, B. R., Bruccoleri, R. E., Olafson, B. D., States, D. J., Swaminathan, S. and Karplus, M., "CHARMM: A Program for Macromolecular Energy, Minimization, and Dynamics Calculations", *J. Comp. Chem.*, Vol. 4, 187-217 (1983).

In general, molecular-mechanics-based scoring functions may closely resemble the objective functions utilized by many stochastic optimization-based docking programs. Such functions typically require atomic (or chemical group) level parameterization of various attributes (e.g., charge, mass, vdW radii, bond equilibrium constants, etc.) based on one or more molecular mechanics force fields (e.g., AMBER, MMFF, OPLS, etc.). In some cases, the relevant parameters for the ligand may also be assigned based on usage of other molecular modeling software packages, e.g., ligand partial charges assigned via use of MOPAC [45], AMPAC [46] or AMSOL [47]. They may also include intramolecular interactions (i.e., self-energy of molecules), as well as long range interactions such as electrostatics. In some cases, the combination of energy terms may again be accomplished via numerical weights optimized for reproduction of test ligand-target complexes.

[45] Stewart, J. J. P., *Quantum Chemistry Program Exchange*, Vol. 10:86 (1990).

[46] Liotard, D. A., Healy, E. F., Ruiz, J. M., and Dewar, M. J. S., *Quantum Chemistry Program Exchange*—no. 506, QCPE Bulletin, Vol. 9: 123 (1989).

[47] AMSOL-version 6.5.1 by G. D. Hawkins, D. J. Giesen, G. C. Lynch, C. C. Chambers, I. Rossi, J. W. Storer, J. Li, D. Rinaldi, D. A. Liotard, C. J. Cramer, and D. G. Truhlar, University of Minnesota, Minneapolis (1997).

Knowledge-based scoring functions were first inspired by the potential of mean force statistical mechanics methods for modeling liquids. Examples include DrugScore [48], PMF [49], and BLEEP [50].

[48] Gohlke, H., Hendlich, M. and Klebe, G., "Knowledge-based Scoring Function to Predict Protein-Ligand Interactions", *J. Mol. Biol.*, Vol. 295, 337-356 (2000).

[49] Muegge, I. and Martin, Y. C., "A general and fast scoring function for protein-ligand interactions—a simplified potential approach.", *J. Med. Chem.*, Vol. 42, 791-804 (1999).

[50] Mitchell, J. B. O., Laskowski, R. A., Alex, A. and Thornton, J. M., "BLEEP—Potential of Mean Force Describing Protein-Ligand Interactions II. Calculation of Binding Energies and Comparison with Experimental Data", *J. Comp. Chem.*, Vol. 20, 1165-1176 (1999).

In general, knowledge-based scoring functions do not require partitioning of the affinity function. However, they do require usage of a large database of 3-D structures of relevant molecular complexes. There is also usually no need for regression against a data set of molecular complexes with known experimental binding affinities. These methods are based on the underlying assumption that the more favorable an interaction is between two atoms, at a given distance, the more frequent its occurrence relative to expectations in a bulk, disordered medium. These schemes are sometimes referred to as 'inverse Boltzmann' schemes, but in fact the presence of local, optimized structures in macromolecules and protein folds means that distance-dependent pair-wise preference distributions need not be strictly Boltzmann. It is also possible to introduce the concept of singlet preferences based on other molecular descriptors, e.g., solvent accessible surface area for approximation of solvation effects.

Hybrid scoring functions may be a mixture of one or more scoring functions of distinct type. One example is VALIDATE [51], which is a molecular-mechanics/empirical hybrid function. Other combinations of scoring functions may include the concept of consensus scoring in which multiple functions may be evaluated for each molecular combination and some form of 'consensus' decision is made based on a set of rules or statistical criteria, e.g., states that occur in the top 10% rank list of each scoring function (intersection-based), states that have a high mean rank (average-based), etc. A useful review discussion of consensus scoring can be found in Bissantz et al. [52].

[51] Head, R. D., Smythe, M. L., Oprea, T. I., Waller, C. L., Green, S. M. and Marshall, G. R., "VALIDATE: A New Method for Receptor-Based Prediction of Binding Affinities of Novel Ligand", *J. American Chemical Society*, Vol. 118, 3959-3969 (1996).

[52] Bissantz, C., Folkers, G., Rognan, D., "Protein-based virtual screening of chemical databases. 1. Evaluation of different docking/scoring combinations", *J Med Chem*, Vol. 43, 4759-4767 (2000). However, none of the current computational tools available for modeling of target-ligand molecular combinations provide both the necessary accuracy and speed as required in today's drug discovery in order to enable the efficient large-scale screening of potential drug candidates.

Various file formats exist for the digital representation of structural and chemical information for both target proteins and compounds as related to structural databases. Examples include the pdb, mol2 (from Tripos), and the SMILES formats.

[53] Westbrook, J. and Fitzgerald, P. M. (2003): *Structural Bioinformatics*, P. E. Bourne and H. Weissig (editors). Hoboken, N.J., John Wiley & Sons, Inc. pp. 161-179.

[54] www.tripos.com/custResources/mol2Files/

[55] www.daylight.com/dayhtml/smiles/smiles-intro.html

[56] Clark, M., Cramer, R. D., Opdenbosch, N. V., "Validation of the General Purpose Tripos 5.2 Force Field", *J. Comp. Chem.*, Vol. 10, 982-1012 (1989).

[57] www2.chemi.e.uni-erlangen.de/software/corina/index.html Molecular representation schemes exist that partition molecules based on chemical, and structural rules.

[58] Xiao Qing Lewell, Duncan B. Judd, Stephen P. Watson, Michael M. Hann; RECAP—Retrosynthetic Combinatorial Analysis Procedure: a powerful new technique for identifying privileged molecular fragments with useful applications in combinatorial chemistry. J. Chem. Inf. Comput. Sci. 1998, 38, 511-522

[59] 2D Overlay with feature trees M. Rarey and J S. Dixon JCAMD, 12: 471-490, 1998.

DETAILED DESCRIPTION

The present invention has many applications, as will be apparent after reading this disclosure. In describing an embodiment of a computational system according to the present invention, only a few of the possible variations are described. Other applications and variations will be apparent to one of ordinary skill in the art, so the invention should not be construed as narrowly as the examples, but rather in accordance with the appended claims.

The present invention relates to partitioning a molecule for the purpose of storing, transmitting, and processing the molecule rapidly and efficiently by processing it in smaller parts, compared to processing the entire molecule without any partitioning. Embodiments of the invention will now be described, by way of example, not limitation. It is to be understood that the invention is of broad utility and may be used in many different contexts.

In the following description the term biopolymer refers to a macromolecule that comprises one or more of a protein, nucleic acid (DNA or RNA), peptide or nucleotide sequence or any portions or fragments thereof. Herein the term biomolecule refers to a chemical entity that comprises one or more of a biopolymer, carbohydrate, hormone, or other molecule or chemical compound, either inorganic or organic, including, but not limited to, synthetic, medicinal, druglike, or natural compounds, or any portions or fragments thereof.

A molecular subset is a whole or parts of the components of a molecule, where the components can be single atoms or bonds, groups of atoms and/or bonds, amino acid residues, nucleotides, etc. A molecular subset might include a molecule, a part of a molecule, a chemical compound composed of one or more molecules (or other bioreactive agents), a protein, one or more subsets or domains of a protein, a nucleic acid, one or more peptides, or one or more oligonucleotides. In another embodiment of the present invention, a molecular subset may also include one or more ions, individual atoms, or whole or parts of other simple molecules such as salts, gas molecules, water molecules, radicals, or even organic compounds like alcohols, esters, ketones, simple sugars, etc. In yet another embodiment, the molecular subset may also include organic molecules, residues, nucleotides, carbohydrates, inorganic molecules, and other chemically active items including synthetic, medicinal, drug-like, or natural compounds.

In yet another embodiment, the molecular subset may already be bound or attached to the target through one or more covalent bonds. In another embodiment the molecular subset may in fact include one or more structural components of the target, such as secondary structure elements that make up a tertiary structure of a protein or subunits of a protein quaternary structure. In another embodiment the molecular subset may include one or more portions of a target molecule, such as protein domains that include the whole or part of an active site, one or more spatially connected subsets of the protein structure that are selected based on proximity to one or more protein residues, or even disconnected protein subsets that feature catalytic or other surface residues that are of interest for various molecular interactions. In another embodiment, the molecular subset may include the whole of or part of an existing molecular complex, meaning a molecular combination between two or more other molecular subset, as, for example, an activated protein or an allosterically bound protein.

A molecular combination (or combination) is a collection of two or more molecular subsets that may potentially bind, form a molecular complex, or otherwise interact with one another, usually in the context of a particular physical, chemical, or biological environment. A combination specifies at the very least the identities of the two or more interacting molecular subsets.

Molecular combination will represent the typical scenario of two molecular subsets where a ligand biomolecule (first molecular subset) interacts with a target biomolecule (usually a biopolymer; second molecular subset). Thus a typical analysis of a molecular combination seeks to determine whether, and to what degree, a ligand will interact with a target molecule in a particular environment. It should be understood that, unless otherwise indicated, such examples and explanations could more generally apply to molecular combinations wherein more than two molecular subsets bind or interact with one another, representing the whole of, or portion(s) of, one or more target molecules and/or one or more ligands, or even other molecules such as those that may be associated with the specified environment.

In another embodiment, the analysis may involve a plurality of molecular combinations, each corresponding to a different ligand, selected, for example, from a molecule library (virtual or otherwise), in combination with the same target molecule in the same environment, in order to find one or more ligands that might bind or otherwise react with the target or even to better characterize the active site of a target protein. In such cases, it may be necessary to assign a score or ranking for each molecular combination in order to achieve relative comparison of relevant bioactivity.

Molecular conformation (or, conformation) denotes the relative positions of all atoms comprising the molecular subset. Note that a conformation does not denote the absolute positions of all atoms comprising the molecular subset. For example, if all atoms in a molecular subset are translated by the same distance in the same direction, then atoms have not changed their position relative to each other, and the conformation after translation is identical to conformation before translation. Similarly, if all atoms are rotated about the same axis by the same angle, there is no change to the conformation. In fact, linear coordinate transformations applied to all constituent atoms will not result in a different molecular conformation. Two different conformations of the same molecular subset may result due to changes in bond lengths, bond angles, bond torsions (both proper and improper), or other more complex changes such as ring transformations (e.g., ring corner flapping, ring book folding, etc.). In many of the forthcoming examples and explanations, it will be assumed that most covalent bonds are preserved during a change in conformation, i.e., bonds are not broken or formed, though this need not be the case for other chemical bonds such as disulfide bonds, hydrogen bonds, and salt bridges. The difference between two conformations may be as subtle (local) as the change in position of only one atom in the subset or as large (global) as the change associated with a distinct protein fold or the alteration of side chains for multiple active residues. Some changes in conformation while geometrically possible are not generally physically realizable as they may result in unfavorable steric clashes of constituent atoms or groups. The allowed changes in conformation are generally termed conformational degrees of freedom.

FIG. 2 shows diagrammatic examples of some of the conformational degrees of freedom associated with changes in molecular conformation. Item 200 shows an example of a chemical bond stretching, i.e., a change in bond length, between two neighboring atoms 201 and 202. Item 210 shows an example of bond angle bending, i.e., a change in bond angle, between three consecutive atoms 211, 212, and 213. Item 220 shows an example of a proper torsion, i.e., a rotation around the bond between atoms 222 and 223, or equivalently a change in the dihedral angle between the plane defined by atoms 221, 222, and 223 and the plane defined by 222, 223 and 224. Note that in this example for a proper torsion it is assumed that atoms 225 and 226 will similarly rotate around the bond between atoms 222 and 223, in order to preserve relative distances with respect to themselves and to atoms 222, 223, and 224.

Continuing with FIG. 2, item 230 shows an example of an improper torsion, i.e., a change in the dihedral angle between the plane defined by atoms 231, 232, and 233 and the plane defined by 231, 232 and 234. Item 240 shows an example of a 'book-folding' transformation of a nonaromatic homocyclic ring defined by atoms 241, 242, 243, 244, 245, and 246. In this case the transformation reflects a change in the angle between the plane defined by atoms 241, 242, 243, and 244 and the plane defined by 241, 246, 245, and 244. Lastly item 250 shows a 'corner-flapping' transformation of the a nonaromatic homocyclic ring, but now the transformation reflects a change in the angle between the plane defined by atoms 251, 252, 253, 255, and 256 and the plane defined by atoms 253, 254, and 255.

Other conformational degrees of freedom are possible such as (but not limited to) the exchange between cis and trans modes, the change in one or more chiral centers, reflecting different stereoisomers, or one or more complicated deformations of rings, especially macrocyclic ones. However, many (if not almost all) changes in molecular conformation that do not break or form covalent bonds can be decomposed into a collection of one or more of the conformational degrees of freedom listed in FIG. 2.

In many cases a degree of freedom may also have constraints that reflect bounds on the permitted motions of relevant atoms and bonds. Such constraints may be motivated by the nature or hybridization state of the chemical bond(s), the energy landscape associated with the structural alteration in question, or even other more sophisticated considerations such as those relating to conservation of secondary structure elements or protein structural motifs or the presence of various heteroatoms or other molecules.

In many of the forthcoming examples and explanations, the conformation of a molecular subset will be dominantly associated with one or more degrees of freedom related to proper and improper torsions, since for many systems the bond lengths and bond angles of most chemical bonds in standard ligands and targets do not change significantly between the unbound and bound states of a combination; the most likely exception being associated with structural perturbations of chemical groups featuring cyclic (especially macrocyclic)

rings. However, it should be obvious to one skilled in the art that molecular conformations need not be limited to torsional degrees of freedom alone.

As a molecular combination may include two or more molecular subsets in a specified environment, the term configuration will be used henceforth in the description to represent the joint poses of all constituent molecular subsets. Thus a particular configuration of a molecular combination describes the set of positions of all structural components of all molecular subsets and all components of the environment with respect to one another, usually in the context of a chosen coordinate system.

A molecular transformation is defined as an operation applied to one and only one conformational degree of freedom that has the capacity to change the molecular conformation. Note that a transformation excludes rigid body transformations of the molecule, because molecular conformation denotes only relative, not absolute, positions of atoms comprising the molecular subset. In one embodiment, some bonds in the molecule might be rotated about some prescribed axis, such that it changes the atomic coordinates of all atoms connected to the rotated bonds. In another embodiment, some bonds in the molecule might be lengthened, thus changing the atomic coordinates of all atoms connected to the bonds. In yet another embodiment, a six-member ring might undergo a book-folding transformation. In an alternate embodiment, the transform might change chirality about one or more of the chiral centers of the molecule.

FIG. 3a shows a 'ball-and-stick' rendering of a conformation 390 of a methotrexate molecule 300 with chemical formula $C_{20}H_{22}N_8O_5$. The molecule consists of a collection of atoms 310 and bonds 350. The small, black atoms, as indicated by item 313, represent carbon atoms. The tiny, white atoms, as indicated by item 316, represent hydrogen atoms, whereas the slightly larger dark atoms (item 310) are oxygen atoms and the larger white atoms (item 320) are nitrogen atoms.

In FIG. 3a, item 323 denotes a circle containing a benzene ring ($C_6H_4$), and item 325 a circle containing a carboxyl group ($COO^-$), and item 327 another circle containing a methyl group ($CH_3$). Item 353 denotes a covalent bond connecting the benzene ring 320 to the ester group that includes the methyl group 327. Item 355 denotes a covalent bond connecting the carbon atom 313 to the carboxyl group 325. Lastly item 357 denotes a covalent bond connecting the methyl group 327 to a nitrogen atom 383.

FIG. 3b shows a 'ball-and-stick' rendering of another conformation 393 of the same methotrexate molecule 300. The conformations in FIGS. 3a and 3b differ only in the value of the torsion angles assigned to the torsional degrees of freedom 355 and 357, thus resulting in different positions for atoms and bonds in the methyl group (327) and the carboxyl group (325) relative to the rest of the molecule. In other words, FIG. 3b results by applying a molecular transformation to FIG. 3a, viz. change to the value of the torsion angles assigned to torsional degrees of freedom 355 and 357. FIG. 3c shows a 'ball-and-stick' rendering of another conformation 396 of the same methotrexate molecule 300 but in this case the differences in conformation are much more dramatic, and the molecular transformation applied to the conformation of FIG. 3a to arrive at the conformation of FIG. 3c also involve changes in bond lengths and angles as well as multiple torsions and a deformation of the benzene ring.

Atoms comprising a molecular subset are said to be invariant with respect to a molecular transformation if their coordinates are not changed by the transformation. Bonds comprising a molecular subset are said to be invariant with respect to a molecular transformation, if the coordinates of atoms that the bond connects, are not changed by the transformation. An example of invariance is shown in FIG. 3b, where 330 is unaffected by dihedral rotations applied to 355 and 357, and is thus invariant with respect to both the transformations. Notice that both 310 and 325 are invariant with respect to the dihedral rotation applied to 357. Similarly, both 310 and 327 are invariant with respect to the dihedral rotation applied to 355. FIG. 3d shows another example of invariance in a methotrexate molecule, in which coordinates of the group of atoms 381 are modified by rotation about bond 385, whereas coordinates of group of atoms 383 remain invariant with respect to the rotation about bond 385.

Typically, a set of appropriate molecular descriptors describing each distinct configuration will be used to distinguish one configuration from another. Molecular descriptors may include, but are not limited to, a) chemical descriptors (e.g., element, atom type, chemical group, residue, bond type, hybridization state, ionization state, tautomeric state, chirality, stereochemistry, protonation, hydrogen bond capacity [i.e., donor or acceptor], aromaticity, etc.); b) physical descriptors (e.g., charge, both formal and partial, mass, polarizability, ionization energy, characteristic size parameters, such as van der Waals [vdW] radii, vdW well depths, hydrophobicity, hydrogen-bonding potential parameters, solubility, equilibrium-bond parameters relating bond energies to bond geometries, etc.; c) geometrical descriptors (e.g., atomic coordinates, bond vectors, bond lengths, bond angles, bond torsions, suitable structural descriptors for rings, descriptors for molecular surfaces and volumes, such as solvent-accessible surfaces and solvent-excluded volumes, etc.

Chemical descriptors may be assigned based on application of one or more rules or concepts of organic (or inorganic, if appropriate) chemistry to representative chemical structures that must at least stipulate basic structural information such as element type and bond connectivity (i.e., which atoms are connected to one another; excluding hydrogens) but may also contain some form of coordinate information. Such chemical structures may be stored and received in a number of different data representations. One common example of data representation, though many others are also possible, is that of a PDB file, for which a full description of the PDB file format can be found Westbrook et al. [53]. Examples of existing software programs that can be used to assign chemical descriptors include SYBYL™ from Tripos, Chimera™ from UCSF, and WhatIf™ (for proteins), etc. Correct assignment of chemical descriptors may also include additional input regarding chiral centers and stereochemistry or even environmental factors, such as expected pH as related to assignment of ionization states.

FIG. 4a shows a pdb file representation 400 of a chemical structure for the methotrexate ligand conformation described in FIG. 3, including a general header 410, a section 420 composed of atom type and coordinate information, and a section 425 regarding bond connectivity information. The header section 410 may contain any annotation or other information desired regarding the identity, source, or characteristics of the molecule and its conformation. Section 420 shows a list of all 33 non-hydrogen atoms of methotrexate and for each atom it includes a chemical type (e.g., atomic element) and three spatial coordinates. For instance, the line for atom 6 shows that it is a nitrogen atom with name NA4 in a compound (or residue if a protein) named MTX in chain A with compound (or residue) ID of 1 and with (x, y, z) coordinates (20.821, 57.440, 21.075) in a specified Cartesian coordinate system. Note that the compound or residue name field may be more relevant for amino or nucleic acid residues in biopolymers.

Section 425 of the PDB file 400, sometimes called the connect record of a PDB file, describes a list of the bonds associated with each atom. For instance, the first line of this section shows that atom 1 is bonded to atoms (2), and (12), whereas the second line shows that atom 2 is bonded to atoms (1), (3), and (4). Notice also how in this example hydrogens are missing and as such the bond connections for each atom may not be complete. Of course, completed variants of the PDB file representation are possible if the positions of hydrogen atoms are already specified, but in many cases where the chemical structure originates from experimental observations the positions of hydrogens may be very uncertain or missing altogether.

FIG. 4b shows a Tripos mol2 file constructed by using SYBYL to assign various chemical descriptors from the PDB file in FIG. 4a. Column 430 lists an index for each atom; column 433 lists an atom name (may be nonunique) for each atom; columns 435, 437, and 439 respectively list x, y, z coordinates for each atom in an internal coordinate system; column 440 lists a SYBYL atom type for each atom; and columns 442 and 445 list a residue ID and a residue name for each atom (relevant for proteins, nucleic acids, etc.). Section 450 lists all bonds in the molecule. Column 451 lists a bond index for each bond; columns 452 and 453 the atom indices of the two atoms connected by the bond; and column 455 the bond type, which may be single, double, triple, delocalized, amide, aromatic, or other specialized covalent bonds. In other embodiments such information may also represent noncovalent bonds such as salt bridges or hydrogen bonds.

In this example, notice how the hydrogen atoms have now been included (and in this case their likely positions predicted) as the result of assignment of chemical descriptors via computational means. In this example, SYBYL atom types contain codified information for hybridization states, chemical type, bond connectivity, hydrogen bond capacity, aromaticity, and in some cases chemical group. Moreover, the ionization states can generally be inferred by a combination of atom types and hydrogenation. Other examples may even include data relevant to lone pairs. In this example, the mol2 file represents a portion of the chemical descriptor data corresponding to the methotrexate ligand.

Physical descriptors depend on one or more chemical descriptors and are typically related to atoms and/or bonds but may also be characterized by chemical group, residue, etc. Values for physical descriptors are typically assigned according to one or more parameter sets associated with molecular mechanics force fields like AMBER [40] [41], OPLS [42], MMFF [43], and CHARMM [44]. Some physical descriptors may also be assigned according to the use of one or more molecular modeling software packages such as the assignment of partial charges via Mopac [45] or AMPAC [46]. The choice of energy interactions to be modeled will typically dictate the type and form of physical descriptors that must be determined for each molecular subset in order to compute affinity for a given molecular combination.

FIG. 4c shows a file containing a subset of physical descriptors assigned via the Amber96 force field (in conjunction with Mopac v7.0 for the partial charges) for the methotrexate ligand corresponding to FIGS. 4a and 4b. Section 460 describes atomic physical descriptors related to charge (column 462), mass (column 463), vdW radius (column 464), and vdW well depth (column 465) for the identical atom names (column 461) originally listed in FIG. 3a. Section 470 describes bond physical descriptors related to the ten allowed bond torsions described in FIG. 2. Here columns 472, 474, 476, and 478 denote standard numerical parameters for a generalized Pitzer potential used in estimating the strain energy associated with dihedral changes. In this example, the file in FIG. 4c represents a portion of the physical descriptor data corresponding to the methotrexate ligand associated with FIGS. 4a and 4b.

Geometrical descriptors relate to the description of structure of one or more components of the molecular combination. This may include, but is not limited to, coordinates or other spatial information relating to points representing positions of atomic centers, vectors representing various bonds, planes representing various chemical groups, spheres representing the extent and placement of individual atoms, 3-D surfaces representing solute-solvent interfaces, volumes representing solute occupancy, spatial 3-D functions representing discretization of interaction fields or potentials onto 3-D volumetric grids (e.g., probe grid maps [26] [31], meshes for differential equation solvers, etc.), or even a generalized set of appropriate geometrical basis functions for approximate representations of structures, surfaces, and/or volumes (e.g., spherical harmonics radial basis functions of Ritchie et al. [13]). Geometrical descriptors may also include one or more geometric variables (e.g., angles, torsions, lengths, etc.) representing one or more allowed degrees of freedom associated with different poses, such as some of the elementary structural transformations described in conjunction with FIG. 2.

Some geometrical descriptors, like for example, those describing points, vectors, planes, and spheres, have natural representations, though the actual values may depend on the choice of coordinate system. Others like surfaces, volumes, grid maps, or basis functions may have various representations depending on the storage requirements, the level of desired precision, and the nature of the object to be represented. As an example, surface may be represented by a series of surface normals or a collection of various elementary surface patches. Volumes may be represented by occupancy of a 3-D bitmap or by a union of simpler geometric objects such as spheres or polygons.

Geometrical descriptors involved with structural degrees of freedom may be continuous or discrete variables, may have one or more constraints imposed by basic structural or energetic considerations, and may depend on the choice of an internal coordinate system for the molecular subset. Such descriptors are of particular importance as they describe the geometrical transformations (or operators) that distinguish two different geometric states of the same molecule or combination (e.g., conformation, pose, configuration).

A molecular subset with its descriptor data can be represented digitally in many ways. In one embodiment, a digital representation for the descriptor data of a molecular subset can be in the form of a text file, such as a pdb file (FIG. 4a) or a mol2 file (FIG. 4b). pdb and mol2 files are representations used for storing molecular data.

Another embodiment of a representation for a molecular subset's descriptors is the list data structure. FIG. 5a shows a schematic representation 500 of a four-peptide pepstatin analog molecule IVVL (isovalryl-valine-valine-lysta-o-ethyl). Each filled circle represents an atom. Lines connecting the circles represent bonds between atoms. A unique number assigned to each circle identifies each distinct atom. The numbers can be assigned arbitrarily and only serve as identification tags for the atoms. The type of the atom represented by each filled circle is also indicated, for example, atom 15 is nitrogen in the valine peptide group 510, atom 12 is a carbon in another valine peptide group 520, atom 5 is a carbon in the isovaleric acid group 530, atom 26 is an alpha-carbon in the statine analog lysta-o-ethyl group, and so on. FIG. 6a shows a 2D schematic representation of the methotrexate molecule shown in FIG. 3a.

An example of a list representation is shown in FIG. 5b, in which some molecular descriptor data for molecule IVVL are represented as a list. Each line in the list contains the index of the atom in the list 501, its atom type 502, its residue 503, and its spatial coordinates 504. FIG. 6b shows a list representation of methotrexate. Each line in the list contains the index of the atom in list 601, its atom type 602, its spatial coordinates 603, and its partial charge 604. Unlike the list representation for IVVL in FIG. 5b, FIG. 6b does not contain the residue type of each atom, and does contain the partial charge for each atom. It should be understood that FIGS. 5b and 6b are illustrative, not exhaustive examples, of how a molecule's descriptor data can be represented as a list.

In yet another embodiment a molecular subset's descriptor data may be represented as a tree. A tree data structure is defined as a collection of objects called nodes and connections between nodes called links. In a tree structure, nodes are distributed at one or more levels, and a node is connected to one or more nodes at the level above itself and to one or more nodes at the level below itself. Nodes at the first level (also known as root nodes) are connected only to nodes at the level below them. Nodes at the last level (also known as leaf nodes) are connected only to nodes at the level above them. A node at a particular level is known as a 'parent' node to one or more nodes it is connected to at the level below, and as a 'child' node to one or more nodes it is connected to at the level above. A first tree is a subtree of a second tree, if the nodes and links of the first tree are also contained in the second tree.

FIG. 5c shows one possible tree representation for the molecule in which nodes represent atoms and links between nodes represent bonds between atoms. Black nodes represent nitrogen atoms, gray nodes represent oxygen atoms, and white nodes represent carbon atoms. Each node's number indicates the atom it represents in FIG. 5a. In the embodiment shown in FIG. 5c, node number 15, a nitrogen atom, is at the top level. Atom 15 is connected to atoms 12 and 19 in FIG. 5a; therefore, node number 15 has links to nodes 12 and 19, which are placed at the second level of the tree. Thus, node 15 is the root node of the tree. Node 15 is also the parent node of nodes 12 and 19, and nodes 12 and 19 are its children nodes. Continuing with the same figure, atom 12 is bonded to atoms 09 and 11 in FIG. 5a; therefore, node 12 is linked to nodes 09 and 11, which are placed at the third level of the tree. The number of levels of the tree depend on the size and structure of the molecule that the tree represents. In FIG. 5c, the tree has eleven levels. Note that the number of nodes at each level need not be the same. The first level contains one node, the fourth level contains six nodes, the sixth level contains four nodes, etc. FIG. 5d shows another tree representation for molecule IVVL of FIG. 5a. In this embodiment of a tree representation, atom 32 is chosen to be at the first level. The representation is clearly very different from the on shown in FIG. 5c. As an example of the differences, the tree in FIG. 5d has eighteen levels, whereas the tree in FIG. 5c has eleven levels. Thus, a tree representation not only depends on the size and structure of the molecule, but also on one or more atoms that are chosen to be at the first level of the tree. It should be understood that there could be several tree representations of a given molecule.

Another example of a tree representation is shown in FIG. 6c. It represents the methotrexate molecule shown in FIG. 6a. Trees are unable to represent closed loops or rings. If it is desired to use a tree to represent structures containing rings, then some bonds need to be omitted from the representation, in order that there are no rings in the representation. For example, methotrexate contains three rings 615, 625, and 635. Its tree representation in FIG. 6c omits bonds between atoms 02 and 04, 05 and 08, and 19 and 23. The omitted bonds are shown as dotted lines in FIG. 6c. The dotted lines are not links but are merely shown to help visualize which bonds are not represented in FIG. 6c. It should be evident to those skilled in the arts that other tree representations are also possible for methotrexate.

In an alternate embodiment, the nodes of a tree can represent molecule fragments rather than atoms. FIG. 7a shows a schematic representation of a methotrexate molecule where the rings are labeled 710, 720. A tree representation of methotrexate is shown in FIG. 7b, for which node 01 represents the pteridine ring 710 and node 11 represents the benzene ring 720.

In yet another embodiment, molecular descriptor data may be represented as a graph. A graph is defined as a collection of objects called nodes and connections between nodes called links. Unlike a tree, a graph may not have its nodes distributed in levels, and a node may be connected to any other node. FIG. 6d shows a graph representation of methotrexate. Each node represents an atom, and a link between nodes represents a bond between atoms. Open circles represent carbon, black circles represent nitrogen, and gray circles represent oxygen in the graph. The number inside each circle corresponds to the number of the atom it represents. For example, node 22 represents the carbon numbered 22 in the benzene ring, and the node numbered 11 represents the nitrogen atom numbered 11 in the pteridine ring. Notice that a graph can represent closed loops or rings, so that all bonds comprising the pteridine ring and the benzene ring are represented in graph. In a tree representation of methotrexate, some of the bonds in the ring had to be omitted from the representation.

In another embodiment of a graph representation of a molecular subset, nodes may represent particular fragments with links connecting those fragments whose constituent atoms are connected in the molecule. FIG. 8a shows a schematic representation of methotrexate and FIG. 8b shows a graph representation of methotrexate. Node 1 in the graph represents the pteridine ring containing item 810, node 11 represents carboxyl group 820, and node 17 represents carboxyl group 830. The link between node 01 and 03, which represents a single carbon atom, represents that an atom comprising node 01 is connected to carbon atom 03.

FIG. 9a shows a schematic representation of a polypeptide comprised of six amino acids (SEQ ID NO:1) MET 910, TYR 920, 930, 940, TRP 950, and PRO 960, with a graph representation for the molecule shown in FIG. 9b. Nodes in the graph represent atoms, and links represent bonds. Notice that the graph has a main chain (also known as backbone) comprised of repeating patterns of O—C—C—N. An example of the repeating pattern is 901, with its constituent atoms being oxygen 911, carbons 913, 915, and nitrogen 917. The main chain also has residues or side chains attached to it. For example, 919 is a side chain composed of the amino acid TRP and corresponds to item 950 in FIG. 9a. The molecule is an example of a small protein; large proteins are long chain of amino acids. A link drawn as a dotted line is part of an aromatic ring, bold lines between carbon and oxygen atoms are aliphatic double bonds, bold lines between nitrogen and carbon are peptide bonds, and thin solid lines are single aliphatic bonds.

It should be evident to a person skilled in the arts that a molecular subset can be represented by a graph data structure in many different ways. The embodiments described above are meant only as illustrative examples.

In a preferred embodiment, a molecular subset's descriptor data is represented as a graph so as to make it convenient to describe operations on molecular subsets. It should also be understood that the data structures mentioned so far—lists, trees, and graphs—are only illustrative examples, not exhaustive ones, of data structures that can be used to represent molecule descriptor data.

We now set forth a few definitions, which will be of utility in further description of the invention.

- A graph is said to be smaller than another graph, if the former contains fewer nodes than the latter.
- A graph is a subgraph of another graph, if the latter contains all nodes of the former.
- Two graphs are said to be unconnected if there is no link between any node of one graph to any node of the other graph.
- Two graphs are said to be independent with respect to a set of transformations, if the transformations applied to any one of the two graphs do not change the coordinates of atoms in the other graph.
- A link is said to be invariant with respect to a set of transformations, if the transformations do not change the coordinates of atoms comprising the nodes that the link connects.

This invention describes a method to divide a molecular subset into smaller parts to facilitate its more efficient storage, transmission, and processing, compared to an undivided molecular subset. We term the process of dividing the molecular representation into smaller parts as partitioning, and the smaller parts of molecular representation as subrepresentations. Two subrepresentations will be termed unconnected if the there is no link connecting any node from one subrepresentation to any node from the other subrepresentation, else the two subrepresentations will be termed connected. Two subrepresentations will be termed mutually independent with respect to a set of transformations, if any of the set of transformations applied to any one of the two subrepresentations do not change the coordinates of any atoms represented by the nodes of the other subrepresentation. Similarly, a subrepresentation is termed invariant with respect to a set of transformations, if any of the set of transformations applied to the subrepresentation do not modify the coordinates of any atoms represented by the nodes of the subrepresentation.

An embodiment of a system for processing molecules is shown in FIG. 10. The first engine in the pipeline 1020 reads molecule information from an input or storage device 1010. The second engine in the pipeline 1030 applies a molecular transformation to the molecule data read by the preceding engine 1020. The output of molecular transformation engine 1030 is sent to downstream processing engines 1040, 1050 in the pipeline. The output of 1050 may go to a storage device or may go to another computational engine.

In one embodiment, the molecular processing system 1000 may be implemented on a dedicated microprocessor, ASIC, or FPGA. In another embodiment, molecular processing system 1000 may be implemented on an electronic or system board featuring multiple microprocessors, ASICs, or FPGAs. In yet another embodiment, molecular processing system 1000 may be implemented on or across multiple boards housed in one or more electronic devices. In yet another embodiment, molecular processing system 1000 may be implemented across multiple devices containing one or more microprocessors, ASICs, or FPGAs on one or more electronic boards and the devices connected across a network.

In some embodiments, molecular processing system 1000 may also include one or more storage media devices for the storage of various, required data elements used in or produced by the analysis. Alternatively, in some other embodiments, some or all of the storage media devices may be externally located but networked or otherwise connected to the molecular processing system 1000. Examples of external storage media devices may include one or more database servers or file systems. In some embodiments involving implementations featuring one or more boards, the molecular processing system 1000 may also include one or more software processing components in order to assist the computational process. Alternatively, in some other embodiments, some or all of the software processing components may be externally located but networked or otherwise connected to the molecular processing system 1000.

As explained in the background discussion, in order to run the pipeline of a molecular processing system 1000 with the greatest efficiency, all stages of the pipeline should have identical pipeline stage intervals. Thus, we need a method to speed up or slow down the molecular transformation engine to match the speed of other faster or slower engines in the pipeline. We can slow down a processing engine simply by idling it for some time, which is clearly wasteful. Alternatively, we can speed up the molecular transformation engine by partitioning molecular data into smaller molecular subsets containing fewer atoms and bonds.

Partitioning a molecular representation into subrepresentations also allows design and implementation of a pipelined molecular processing system 1000 with smaller storage and transmission requirements. This enables the system to process molecules equally efficiently regardless of their size.

Partitioning will also be constrained by the actual design of the transform engine and other processing engines. An example of such a constraint due to the design of a device is the amount of available storage in the computational system, such that partitioning is constrained to produce subrepresentations, each of which uses less storage than a predetermined maximum amount. Another example of a constraint due to device design is the amount of available bandwidth between storage devices and processing engines in the molecular processing system, such that partitioning is constrained to produce subrepresentations, each of which can use no more than a predetermined amount of bandwidth. In yet another example, subrepresentations must be produced subject to the constraint that no subrepresentation can use more bandwidth than is available between the plurality of processing engines in a molecular processing system. In an alternate example, the partitioning may be constrained by the total number of available processing engines and the total number of computations that can be performed per cycle in the molecular processing system. Here number of computations means the number of elementary operations such as addition, subtraction, multiplication, division, modulus, bitwise and-ing, bitwise or-ing, etc can be performed per cycle by one or more pipeline stages of the molecular processing system. Thus, the partitioning process may be constrained to produce subrepresentations such that the number of computations associated with each subrepresentation is less than a maximum number.

We define a unit of storage (or, storage unit) as the maximum amount of storage that can participate in one transaction. For example, in some Random Access Memory (RAM) technologies, storage is arranged in groups of bits, and one and only one group of bits can be read or written in one transaction with the memory. In such a case, a storage unit is the size of the group that can be read or written with one transaction. Let us say that the size of such a group in an example of RAM technology is 64 bits. If less than 64 bits, say 40 bits, need to be read, then the technology still returns 64 bits, of which 24 bits will be ignored. If more than 64 bits need to be read, say 100 bits, it will take two transactions to read all 100 bits. Thus, the maximum amount of storage that can be read in one transaction is 64 bits, which is also the size of a unit of storage. In another example, in a storage technology such as disk drives, it may be possible to read one and only one sector of the disk, making the sector a unit of storage. In yet another example, a database may be so configured as to enable read/write of a fixed amount of data for every transaction. In such a case, the limit imposed by the database determines a unit of storage.

We also define a representation storage unit as the amount of storage used to store one subrepresentation. Notice that the amount of storage needed by a subrepresentation may be different from the amount of storage actually used. If such is the case, some part of a representation storage unit will be left unused. For example, let a representation storage unit be 1 Mb, and the amount of storage needed for one subrepresentation be 0.8 Mb. In such a case, the remaining 0.2 Mb is left unused. The unused storage is not used to store all or part of a subrepresentation. In another example, if the amount of storage needed for one subrepresentation is 1.6 Mb, then two representation storage units are used, of which 0.4 Mb is left unused.

The size of a representation storage unit can be used as a constraint on partitioning. For example, if a subrepresentation needs more storage than a representation storage unit, then it is partitioned further. In another example, partitioning may be so constrained such that the total amount of unused storage, summed for all representation storage units in use, is minimized.

We define a unit of transmission (or, transmission unit) as the maximum amount of data that can be transmitted across a transmission channel in one transaction. In one example, in transmitting digital data from Random Access Memory (RAM) to a microprocessor, the maximum amount of data that can be transmitted in a single clock cycle depends on the number of pins on the microprocessor. For example, if 128 pins are dedicated to reading data from RAM, then transmission unit size is 128 bits. If in an instance of channel use 128 bits need to be transmitted across the channel, then the channel is used most efficiently. If less than 128 bits, say only 100 bits, need to be transmitted, the channel still transmits 128 bits, of which 28 bits are ignored by the receiver. Thus, the efficiency of such transmission is less than 100%. If more than 128 bits, say 200 bits, need to be transmitted, then the first transaction contains only a maximum of 128 bits, thus setting the size of the transmission unit. In another example, if the microprocessor of the previous example can be so constructed that in one transaction it can read 256 bits using only 128 pins, then the transmission unit will be 256 bits. In yet another example, if a disk drive controller for reading digital data from a disk drive can read 1 KB in one transaction, then the transmission unit is 1 KB. In yet another example, the receiver may read data from the channel 1 bit at a time, i.e., serially, but the data may have to be transmitted on the channel in groups of bits, i.e., packets, of a predetermined size or range of sizes. In such case, the size of a single transaction is 1 packet and the size of one packet determines a transmission unit. Examples of such a scheme are Ethernet, TCP/IP, etc.

We also define a representation transmission unit as the amount of transmission bandwidth used to transmit one subrepresentation. Notice that the amount of bandwidth needed by a subrepresentation may be different from the amount of bandwidth actually used. If such is the case, some part of a representation transmission unit will consist of bits that are not read by the receiver of the transmission channel, i.e., unread bits. Unread bits can also be said to convey no information. For example, let a representation transmission unit be 1 Mb, and the amount needed for one subrepresentation be 0.8 Mb. In such a case, 0.2 Mb of transmission consists of unread bits. In another example, if the bandwidth needed for one subrepresentation is 1.6 Mb, then two representation transmission units are used, of which 0.4 Mb are left unread.

The size of a representation transmission unit can be used as a constraint on partitioning. For example, if a subrepresentation needs more bandwidth than a representation transmission unit, then it is partitioned further. In another example, partitioning may be so constrained such that the total amount of unread bits, summed for all representation transmission units in use, are minimized.

In the preferred embodiment of the partitioning engine 1020, a series of graph partitioning operators are applied to a molecular representation to produce a number of subrepresentations. The partitioning operators produce a number of subrepresentations subject to some supplied partitioning criteria. After the application of a partitioning operator, each resulting subrepresentation is further evaluated, using one or more partitioning criteria, if it needs further partitioning. One example criterion for further partitioning a subrepresentation is that the subrepresentation has fewer atoms than a predetermined threshold. Another example criterion is that the subrepresentation exceeds a predetermined data storage limit. Yet another example criterion is that the number of subrepresentations generated by the previous partitioning operator was less than a predetermined maximum threshold, and/or greater than a predetermined minimum threshold. An alternate example criterion is that the number of molecular processing computations, including transformations, associated with each subrepresentation is less than a predetermined maximum number and/or greater than a predetermined minimum number. Another example criterion is that the variation in the number of atoms in subrepresentations should be minimized. That is, as far as possible, all subrepresentations should have the same number of atoms. It should be clear to one skilled in the arts that the criteria above are shown merely as illustrative examples.

In the ensuing discussion, we will need to partition a graph into smaller graphs. We define the following kinds of graph partitioning operators to subdivide graphs into smaller graphs.

Link removal operator: This operator removes links from a graph, subject to one or more supplied criteria. Removal of one or more links from a graph may result in dividing the graph into more than one unconnected subgraphs. One or more of the supplied criteria may specify which types of links are to be removed, for example, only invariant links are to be removed, or only links between specific pairs of atoms (say, two carbon atoms) can be removed. Other criteria may specify the constraints that the resulting subgraphs have to satisfy, for example, all subgraphs resulting from link removal should have less than a threshold number of nodes. Examples of criteria that might be supplied to the link removal and the following operators are provided later in the description as partitioning criteria.

An example of the link removal operator is shown in FIG. 11. FIG. 11*a* shows a graph representation of a hypothetical molecule. Nodes of the graph represent atoms and molecule fragments, and links represent bonds. Bold lines represent invariant links, whereas other links are not invariant. FIG. 11*b* shows the result of applying the link removal operator to the graph of FIG. 11*a*. The operator, in this case, removes two links 1101, 1102, resulting in three unconnected subgraphs 1110, 1120, 1130. If each subgraph 1110, 1120, and 1130 is judged to be acceptable by the supplied partitioning criteria, the partitioning is considered complete. If the subgraphs are deemed unacceptable, another set of links are removed, and the resulting subgraphs judged against the supplied criteria.

FIG. 12a shows a schematic of a polypeptide MYWYPY (SEQ ID NO:1). Invariant links are also shown 1210, 1220, 1230, 1240, and 1250 in FIG. 12a. The link removal operator decides to remove all invariant links resulting in six subgraphs 1211, 1221, 1231, 1241, 1251, 1261. FIG. 12b shows an application of the link removal operator which decides to remove only three of the invariant bonds 1220, 1230, 1240, resulting in only three subgraphs 1212, 1222, 1232, 1242. Which of the two partitions is more acceptable is decided by the supplied partitioning criteria.

Invariant link removal operator: This operator performs exactly the same as the link removal operator defined above, with the additional property that all links that are removed must be invariant. We define this operator explicitly, as it will be referred to later in the description.

Node cleaving operator: Like the link removal operator, this operator attempts to split a graph into unconnected subgraphs, subject to the supplied criteria. This operator first chooses a node as the root node, according to one or more supplied constraints. One or more subgraphs that are linked at the root node are split into unconnected graphs as shown in the FIG. 13. FIG. 13a shows a graph representation of a hypothetical molecule, with nodes representing molecular fragments, and links representing bonds. Let us say that the node cleaving operator chooses 1310 as the root node, according to the supplied constraints. FIG. 13b shows the results of cleaving at the chosen root node 1310, to produce three unconnected subgraphs 1320, 1330, and 1340. Notice that the original root node 1310 is now a member of all three resulting subgraphs. Continuing with the example in FIG. 13c, the node could have been cleaved into two parts 1301, 1302, instead of three. Which of the two cleaving results are accepted is determined by the supplied constraints.

If it is not possible to split a graph into unconnected subgraphs, one or more links are removed in order to attempt splitting the graph into subgraphs. FIG. 14a shows a schematic representation of a hypothetical molecule. FIG. 14b shows the result of applying the node cleaving operator to 1410—the graph is not divided into unconnected graphs. In order to construct unconnected subgraphs 1430, 1440, the operator removes link 1420.

In another example, FIG. 15a shows the schematic of a molecule CH2-CBG-ASN-TYR-CH2-PRO-ILE-VAL-NH. FIG. 15b shows the result of cleaving at node 1510—the molecule is not partitioned into two unconnected subgraphs. FIG. 15c shows that removing a link 1520 results in two unconnected subgraphs 1530, 1540.

If it proves to be impossible to split the graph, then no splitting is done at all. The result of applying the node cleaving operator to the input graph, is the input graph itself.

In FIG. 16, the embodiment of the system of the present invention comprises a pipeline, in which the first stage 1610 receives a digital representation of a molecule. The molecule representation is then partitioned into a plurality of subrepresentations by the partitioning engine 1620. The subrepresentations are then processed by one or more molecular subset processing engines 1630. In one embodiment the processing engines may compute molecular transformations on the subrepresentations. In another embodiment the processing engines may compute an affinity function on the atoms and bonds in the subrepresentations. It should be understood that the embodiments of processing engines 1630 described above are meant to be illustrative, not exhaustive.

We now describe the preferred embodiment of the partitioning engine 1620. The input digital representation of the molecule is first used to construct a graph representation of the molecule. It should be evident to one skilled in the arts that in other embodiments of molecular representations data structures such as trees, lists, etc can be also used to construct representations as useful as graphs.

In one embodiment of the partitioning engine, one or more partitioning criteria are applied to the graph representation of the molecule to evaluate whether the graph should be partitioned at all. In an example, the graph may consist of less than a threshold number of nodes, and may not need to be partitioned. In another example, the storage needed by the graph may exceed the maximum allocated storage for a single partition, and may need to be partitioned. If the graph does not need to be partitioned, then the partitioning process is complete. If the graph needs to be partitioned, then it is subjected to the invariant link removal operator.

The invariant link removal operator is applied to the graph, subject to one or more partitioning criteria. Application of the operator produces one or more subrepresentations. Only one subrepresentation may be produced, if the operator can find no manner of partitioning the graph such that one or more of the resultant subrepresentations satisfy the supplied partitioning criteria. Otherwise, more than one subrepresentations are produced. Further partitioning criteria are applied to the resultant subrepresentations to determine which subrepresentations are not partitioned further, and which ones are subjected to the next partitioning operator—node cleaving.

It is possible that all resultant subrepresentations from the invariant link removal step satisfy the desired partitioning criteria, and do not need to be partitioned further. If such is the case, the partitioning process is considered complete.

The node cleaving operator is applied to one or more of the subrepresentations resulting from invariant link removal, subject to one or more partitioning criteria. Application of the operator produces one or more subrepresentations. As with the previous step, only one subrepresentation may be produced, if the operator can find no manner of partitioning the subrepresentations such that one or more of the resultant subrepresentations satisfy the supplied partitioning criteria. Otherwise, more than one subrepresentations are produced. Further partitioning criteria are then applied to the subrepresentations to determine which of the subrepresentations are not partitioned further and which ones are subjected to further partitioning.

It is possible that all resultant subrepresentations from the node cleaving step satisfy the desired partitioning criteria, and do not need to be partitioned further. If such is the case, the partitioning process is considered complete.

Subrepresentations at this stage are partitioned by applying the link removal operator and the node cleaving operator, such that the resulting subrepresentations satisfy the desired partitioning criteria. Notice that the link removal operator can remove any type of links, including invariant links. Links are removed and nodes are cleaved such that unconnected subrepresentations are produced that satisfy the desired partitioning criteria. Subrepresentations produced at this stage are not constrained to be independent, only unconnected. The partitioning process is now considered complete.

The invention described in this disclosure is of wide applicability in molecular processing. Here molecular processing means determining or characterizing one or more molecular combinations via computational means. In some embodiments, this may include, but is not limited to, prediction of likelihood of formation of a potential molecular complex, or a proxy thereof, the estimation of the binding affinity or binding energy between molecular subsets in an environment, the prediction of the binding mode (or even additional alternative modes) for the molecular combination, or the rank prioritization of a collection of molecular subsets (e.g., ligands) based on predicted bioactivity with a target molecular subset, and would therefore also include usage associated with computational target-ligand docking and scoring.

We now describe an embodiment of a possible use of the invention in virtual screening. In this embodiment, quick and efficient calculations of molecular transformations and energies are done as part of an optimization algorithm aimed at finding the best binding mode for a ligand with a target, often a protein. Both the ligand and the protein are partitioned in order to rapidly and efficiently generate many new conformations of the input molecule. Molecular data is received by a processing engine, which partitions the molecule into smaller partitions. Transformations such as proper and improper torsions, dihedral rotations, bond lengthening, and bond angle changes, are applied to one or more bonds in each partition, to generate new conformations for the molecule in a parallel fashion. As partitions are transformed in parallel by several molecular transformation engines, new conformations are generated very rapidly. A number of conformations are generated, each different from the other. Each transformed partition from each conformation is sent to an affinity calculation engine, which calculates the affinity of that particular partition with the target molecule. The partitions are of such size and structure that the cost of computing the transformations, as well as affinities, is constant across partitions enabling the pipeline to be maximally utilized. Conformations are ranked based on a function of the calculated affinities and the worst few are discarded. The remaining molecules are used to generate new conformations, for which affinities are calculated, and so on.

The optimization process is halted when one or more pre-determined halting criteria are met. An example of a simple halting criterion is that the total number of conformations generated throughout the optimization process meets a pre-determined threshold. Another example of a halting criterion is that the number of iterations have reached a predetermined threshold.

What is claimed is:

1. A method for improving computational efficiency in computing measures of a biomolecule's suitability as a lead candidate for a target using a circuit having a plurality of storage units each having a maximum size of storage available, the method comprising:

receiving, at a partitioning engine of the circuit, a molecular representation of a molecular subset of the biomolecule or the target or both, the molecular subset comprising a plurality of atoms and bonds;

receiving, at the partitioning engine, a set of molecular transformations for all or at least one part of the molecular representation, wherein the set of molecular transformations includes at least one rotation operator;

receiving, at the partitioning engine, a set of partitioning operators and a set of partitioning criteria, wherein the partitioning criteria includes the indication of maximum size of a storage unit of the circuit;

partitioning, with the partitioning engine, the molecular representation into a plurality of resultant subrepresentations, wherein the partitioning depends on the set of molecular transformations, the set of partitioning operators, the set of partitioning criteria, and the maximum size of each of the plurality of storage units of the circuit, and wherein the partitioning is further based on an amount of unused storage space for storing each subrepresentation into a respective storage unit such that, by partitioning, the amount of unused storage space of the plurality of storage units of the circuit is reduced; and computing a binding affinity between at least part of the biomolecule and at least part of the target, wherein computing the binding affinity includes performing a calculation involving the molecular subset using a processor, wherein the calculation includes computing molecular transformations for respective resultant subrepresentations that resulted from partitioning the molecular representation into the plurality of resultant subrepresentations, and wherein the binding affinity corresponds to the biomolecule's suitability as a lead candidate.

2. The method of claim 1, wherein the molecular representation is a graph, and the resultant subrepresentations are subgraphs.

3. The method of claim 2, wherein the resultant subrepresentations are connected subrepresentations of the molecular representation.

4. The method of claim 1, wherein the molecular representation is a tree, and the resultant subrepresentations are subtrees.

5. The method of claim 1, wherein one or more of the resultant subrepresentations are invariant with respect to all molecular transformations associated with all remaining subrepresentations.

6. The method of claim 1, wherein the set of molecular transformations include one or more molecular transformations that correspond to proper torsions and one or more molecular transformations that correspond to improper torsions.

7. The method of claim 1, wherein the set of molecular transformations include one or more molecular transformations that correspond to changes in the length of one or more bonds.

8. The method of claim 1, wherein the set of molecular transformations include one or more molecular transformations that correspond to changes in the bond angle between two consecutive bonds.

9. The method of claim 1, wherein the set of molecular transformations include one or more molecular transformations that correspond to a change in chirality about a chiral center.

10. The method of claim 1, wherein the set of molecular transformations include one or more molecular transformations that correspond to a book-folding transformation applied to one or more rings.

11. The method of claim 1, wherein the set of molecular transformations include one or more molecular transformations that correspond to a corner-flapping transformation applied to one or more rings.

12. The method of claim 1, wherein the set of partitioning operators includes an operator that removes invariant links.

13. The method of claim 12, wherein the invariant link removal operator is applied to a molecular representation for a molecular subset including all or part of a polypeptide or a part of a polypeptide, and wherein the removed links correspond to peptide bonds.

14. The method of claim 13, wherein the resultant subrepresentations are such that a side chain exists in no more than one subrepresentation.

15. The method of claim 14, wherein the resultant subrepresentations are such that a subrepresentation may include part of the main chain of the polypeptide.

16. The method of claim 12, wherein the invariant link removal operator is applied to a molecular representation for molecular subset including all or part of a nucleotide.

17. The method of claim 1, wherein partitioning of the molecular representation comprises:
removing invariant links subject to a first set of partitioning criteria, resulting in one or more first subrepresentations;
subsequent to removing invariant links, applying a node cleaving operator, subject to a second set of partitioning criteria, to one or more of the first subrepresentations, resulting in further subrepresentations, and
following applying a node cleaving operator, removing any type of additional links and cleaving additional nodes subject to a final set of criteria, resulting in a final set of subrepresentations.

18. The method of claim 17, wherein all of the first subrepresentations, resulting from removing invariant links subject to the first set of partitioning criteria, satisfy all of the partitioning criteria, and are not partitioned further.

19. The method of claim 17, wherein all further subrepresentations, resulting from application of the node cleaving operator subject to the second set of partitioning criteria, satisfy all of the partitioning criteria, and are not partitioned further.

20. The method of claim 1, wherein the set of partitioning operators includes an operator that performs node cleaving.

21. The method of claim 1, wherein the partitioning criteria include a criterion stipulating that the total number of resultant subrepresentations be less than a predetermined maximum number.

22. The method of claim 1, wherein the partitioning criteria include a criterion stipulating that the total number of resultant subrepresentations is greater than a predetermined minimum number.

23. The method of claim 1, wherein the partitioning criteria include a criterion stipulating that one or more partitions have less than a predetermined maximum number of atoms and/or bonds.

24. The method of claim 1, wherein the partitioning criteria include a criterion stipulating that the number of molecular transformations associated with each subrepresentation is less than a predetermined maximum number.

25. The method of claim 1, wherein the partitioning criteria include a criterion stipulating that the number of molecular transformations associated with each subrepresentation is greater than a predetermined minimum number.

26. The method of claim 1, wherein the partitioning criteria include a criterion stipulating that the variation between the number of atoms in subrepresentations is minimized.

27. The method of claim 1, wherein determining the binding affinity includes computing an affinity function between two or more molecular subsets in a molecular configuration.

28. The method of claim 1, wherein determining the binding affinity provides an analysis of molecular combinations.

29. The method of claim 1, wherein performing the calculation includes generating new molecular conformations using molecular transformations.

30. The method of claim 1, wherein the partitioning criteria include a criterion stipulating that the storage required for each subrepresentation is less than a predetermined maximum amount, and wherein partitioning is constrained such that the total amount of unused storage for storing the plurality of subrepresentations in the plurality of storage units is minimized.

31. The method of claim 30, wherein the minimization of the total amount of unused storage for storing the plurality of subrepresentations in the plurality of storage units is performed as part of an attempt to satisfy all of the partitioning criteria.

32. The method of claim 30, wherein each of a plurality of storage units of the circuit have the same maximum storage size.

33. The method of claim 1, wherein the partitioning criteria include a criterion stipulating that the bandwidth required to transmit each subrepresentation from one device of the circuit to another device of the circuit is less than a predetermined maximum number.

34. The method of claim 1, wherein the partitioning of the molecule representation depends on the bandwidth available between one or more storage devices and one or more processing engines of the circuit.

35. The method of claim 1, wherein the partitioning depends on the bandwidth available between a plurality of processing engines of the circuit.

36. The method of claim 1, wherein the partitioning depends on the number of available processing engines of the circuit.

37. The method of claim 36, wherein the available processing engines can perform a maximum number of computations per cycle.

38. The method of claim 36, wherein the set of partitioning criteria include a criterion stipulating that the number of computations associated with each resultant subrepresentation is less than a predetermined maximum number.

39. The method of claim 1, wherein the partitioning depends on the amount of available storage in the circuit.

40. The method of claim 1, further comprising storing each of the resultant subrepresentations in more than one storage unit.

41. The method of claim 1, further comprising storing each subrepresentation in a representation storage unit, such that a predetermined integral number of representation storage units are stored in one storage unit.

42. The method of claim 41, wherein the integral number depends on the molecular subset.

43. The method of claim 1, wherein each of the resultant subrepresentations is transferred between one or more components of the circuit in more than one transmission unit.

44. The method of claim 43, wherein each subrepresentation is transferred per representation transmission unit, such that a predetermined integral number of transmission units are transferred in one transmission unit.

45. The method of claim 44, wherein the integral number depends on the molecular subset.

46. The method of claim 1, wherein computing molecular transformations for respective resultant subrepresentations includes:
transforming coordinates of at least one of the resultant subrepresentations such that the coordinates are changed.

47. The method of claim 1, wherein the resultant subrepresentations provide a cost of computing the transformations that is more constant across the respective resultant subrepresentations than if said partitioning was not done.

48. The method of claim 1, further comprising:
storing a plurality of the resultant subrepresentations in a memory of the circuit.

49. A molecular processing system, including for use in improving computational efficiency in computing measures of a biomolecule's suitability as a lead candidate for a target, the molecular processing system comprising:
a read data engine that receives a molecular representation of a molecular subset of the biomolecule or the target or both, the molecular subset including a plurality of atoms and bonds;
one or more storage modules each having a maximum size of storage available for storing:
a set of molecular transformations for all or at least one part of the molecular representation, wherein the set of molecular transformations includes at least one rotation operator;
a set of partitioning operators; and
a set of partitioning criteria, wherein the partitioning criteria includes a maximum size of the storage module;
a molecule partitioning engine coupled with the read data engine and the storage modules, wherein the molecule partitioning engine is configured to partition the molecular representation into a plurality of resultant subrepresentations based on the set of molecular transformations, the set of partitioning operators the set of partitioning criteria, and the maximum size of each of the plurality of storage modules, and wherein the partitioning is further based on an amount of unused storage space for storing each subrepresentation into a respective storage module such that, by partitioning, the amount of unused storage space of the plurality of storage modules of the circuit is reduced;
one or more molecular transform engines for transforming at least one of the resultant subrepresentations that resulted from partitioning the molecular representation into the plurality of resultant subrepresentations; and
one or more molecular subset processing engines that compute binding affinity between at least part of the biomolecule and at least part of the target, wherein computing the binding affinity includes performing a calculation involving the molecular subset, the calculation using an output of the one or more molecular transform engines, and wherein the binding affinity corresponds to the biomolecule's suitability as a lead candidate.

50. The molecular processing system of claim 49 wherein the read data engine is configured to receive the set of molecular transformations, the set of partitioning operators and the set of partitioning criteria.

51. The molecular processing system of claim 49 wherein the circuit is an integrated circuit.

52. The molecular processing system of claim 49 wherein the molecule partitioning engine is configured to partition the molecular representation by using an operator that removes invariant links.

53. The molecular processing system of claim 49 wherein the molecule partitioning engine is configured to partition the molecular representation by:
removing invariant links subject to a first set of partitioning criteria, resulting in one or more first subrepresentations;
subsequent to removing invariant links, applying a node cleaving operator, subject to a second set of partitioning criteria, to one or more of the first subrepresentations, resulting in further subrepresentations, and
subsequent to applying a node cleaving operator, removing any type of additional links and cleaving any additional nodes subject to a final set of criteria, resulting in a final set of subrepresentations.

54. The molecular processing system of claim 49 wherein the molecule partitioning engine is configured to partition the molecular representation such that the total number of resultant subrepresentations is less than a predetermined maximum number.

55. The molecular processing system of claim 49 wherein the molecule partitioning engine is configured to partition the molecular representation such that a storage required for each subrepresentation is less than a predetermined maximum amount.

56. The molecular processing system of claim 49 wherein the molecule partitioning engine is configured to partition the molecular representation based on a bandwidth available between the molecular subset processing engines in the molecular processing system and between one or more storage devices and one or more of the molecular subset processing engines.

57. The molecular processing system of claim 49 wherein the molecule partitioning engine is configured to partition the molecular representation based on the number of available molecular subset processing engines and based on a total number of computations that can be performed per cycle in the molecular processing system.

58. The molecular processing system of claim 49, wherein partitioning is constrained such that the total amount of unused storage for storing the plurality of subrepresentations in the plurality of storage units is minimized.

* * * * *

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:synthetic
      six amino acid polypeptide example of a small protein

<400> SEQUENCE: 1

Met Tyr Trp Tyr Pro Tyr
 1               5
```